US00RE39571E

(19) United States
(12) Reissued Patent
Cargill

(10) Patent Number: US RE39,571 E
(45) **Date of Reissued Patent: *Apr. 17, 2007**

(54) METHODS AND APPARATUS FOR SYNTHESIZING LABELED COMBINATORIAL CHEMISTRY LIBRARIES

(75) Inventor: John Cargill, San Diego, CA (US)
(73) Assignee: Nexus Biosystems, Inc., Poway, CA (US)

( * ) Notice: This patent is subject to a terminal disclaimer.

(21) Appl. No.: 10/841,421

(22) Filed: May 7, 2004

Related U.S. Patent Documents

Reissue of:
(64) Patent No.: 6,417,010
Issued: Jul. 9, 2002
Appl. No.: 09/261,718
Filed: Mar. 3, 1999

U.S. Applications:

(62) Division of application No. 08/383,766, filed on Feb. 2, 1995, now Pat. No. 6,087,186.

(51) Int. Cl.

| | |
|---|---|
| ***G01N 33/543*** | (2006.01) |
| ***C12Q 1/68*** | (2006.01) |
| ***G08B 13/14*** | (2006.01) |
| ***A61K 38/00*** | (2006.01) |

(52) U.S. Cl. ..... 436/518; 436/523; 436/526; 436/527; 436/524; 436/525; 436/528; 435/6; 435/DIG. 1; 435/DIG. 9; 435/DIG. 14; 435/DIG. 21; 435/DIG. 29; 435/DIG. 34; 435/DIG. 49; 530/334; 235/439; 340/572.1; 455/92

(58) Field of Classification Search ..... 435/6, 435/287.1, DIG. 1, DIG. 14, DIG. 21, DIG. 34, 435/DIG. 49, DIG. 9, DIG. 29; 436/518, 436/523, 524, 525, 526, 527, 528; 536/24.3; 422/68.1; 369/13.01; 530/334
See application file for complete search history.

(56) References Cited

U.S. PATENT DOCUMENTS

| | | | |
|---|---|---|---|
| 4,631,211 | A | 12/1986 | Houghten |
| 4,713,326 | A | 12/1987 | Dattagupta et al. |
| 4,857,893 | A | 8/1989 | Carroll |

(Continued)

FOREIGN PATENT DOCUMENTS

| | | |
|---|---|---|
| DE | 43 13 807 | 11/1933 |
| DE | 27 24 466 | 12/1978 |
| EP | 0 637 750 | 2/1995 |
| FR | 2 555 744 | 5/1985 |
| GB | 1 423 185 | 1/1976 |
| GB | 2 129 551 A | 5/1984 |
| WO | WO 89/08264 | 9/1989 |

OTHER PUBLICATIONS

Moran, "Radio Frequency Tag Encoded Combinatorial Library Method for the Discovery of Tripeptide–Substituted Cinnamic Acid Inhibitors of the Protein Tyrosine Phosphatase PTP1B," J. Am. Chem. Soc., 1995, 10787–10788, 117, American Chemical Society.

*Primary Examiner*—Padmashri Ponnaluri
(74) *Attorney, Agent, or Firm*—Eleanor M. Musick; Procopio Cory Hargreaves & Savitch LLP

(57) ABSTRACT

The present invention provides labeled synthetic libraries of random oligomers and methods and apparatus for generating labeled synthetic oligomer libraries. Each member of such a library is labeled with a unique identifier tag that specifies the structure or sequence of the oligomer. In a preferred embodiment of the present invention the identifier tag is a microchip that is pre-encoded or encodable with information that is related back to a detector when the identifier tag is pulsed with electromagnetic radiation.

14 Claims, 7 Drawing Sheets

U.S. PATENT DOCUMENTS 5,148,404 A 9/1992 Hilferink et al.
5,214,409 A 5/1993 Beigel
5,262,772 A 11/1993 Urbas et al.
5,308,967 A 5/1994 Jurisch
5,424,186 A 6/1995 Fodor et al.
5,463,564 A 10/1995 Agrafiotis et al.
5,573,905 A 11/1996 Lerner et al.
5,770,455 A * 6/1998 Cargill et al.
5,789,162 A 8/1998 Dower et al.
6,087,186 A 7/2000 Cargill et al.
6,331,273 B1 * 12/2001 Nova et al. ..... 422/68.1
6,352,854 B1 * 3/2002 Nova et al. ..... 435/287.1

* cited by examiner

METHODS AND APPARATUS FOR SYNTHESIZING LABELED COMBINATORIAL CHEMISTRY LIBRARIES

Matter enclosed in heavy brackets [ ] appears in the original patent but forms no part of this reissue specification; matter printed in italics indicates the additions made by reissue.

CROSS REFERENCE TO RELATED APPLICATIONS

The present application is a continuation of application Ser. No. 08/383,766, filed Feb. 2, 1995, now issued as U.S. Pat. No. 6,087,186[, which is a continuation-in-part of application Ser. No. 08/180,863 filed Jan. 13, 1994, now abandoned, which is a continuation in part of application Ser. No. 08/092,862 filed Jul. 16, 1993, now abandoned]. This application is also related to application Ser. No. 08/480,438, filed Jun. 7, 1995, now issued as U.S. Pat. No. 5,770,455, which is a divisional of application Ser. No. 08/383,766.

FIELD OF THE INVENTION

The present invention relates to labeled combinatorial synthesis libraries and methods and apparatus for labeling individual library members of a combinatorial synthesis library with unique identification tags that facilitate elucidation of the structures of the individual library members synthesized.

BACKGROUND OF THE INVENTION

The relationship between structure and function of molecules is a fundamental issue in the study of biological systems. Structure-function relationships are important in understanding, for example, the function of enzymes, cellular communication, and cellular control and feedback mechanisms. Certain macromolecules are known to interact and bind to other molecules having a specific three-dimensional spatial and electronic distribution. Any macromolecule having such specificity can be considered a receptor, whether the macromolecule is an enzyme, a protein, a glycoprotein, an antibody, an oligonucleotide sequence of DNA, RNA or the like. The various molecules that receptors bind are known as ligands.

Pharmaceutical drug discovery is one type of research that relies on the study of structure-function relationships. Most contemporary drug discovery involves discovering novel ligands with desirable patterns of specificity for biologically important receptors. Thus, the time necessary to bring new drugs to market could be greatly reduced by the discovery of novel methods which allow rapid screening of large numbers of potential ligands.

Since the introduction of solid phase synthesis methods for peptides and polynucleotides new methods employing solid phase strategies have been developed that are capable of generating thousands, and in some cases even millions, of individual peptide or nucleic acid polymers using automated or manual techniques. These synthesis strategies, which generate families or libraries of compounds, are generally referred to as "combinatorial chemistry" or "combinatorial synthesis" strategies.

Combinatorial chemistry strategies can be a powerful tool for rapidly elucidating novel ligands to receptors of interest. These methods show particular promise for identifying new therapeutics. See generally, Gorgon et al., "Applications of Combinatorial Technologies to Drug Discovery: II. Combinatorial Organic Synthesis, Library Screening Strategies, and Future Directions," J. Med. Chem 37:1385–401 (1994) and Gallop et al., "Applications of Combinatorial Technologies to Drug Discovery: I. Background and Peptide Combinatorial Libraries," J. Med. Chem 37:1233–51 (1994). For example, combinatorial libraries have been used to identify nucleic acid aptamers, Latham et al., "The Application of a Modified Nucleotide in Aptamer Selection: Novel Thrombin Aptamers Containing 5-(1-Pentynyl)-2'-Deoxy Uridine," Nucl. Acids Res. 22:2817–2822 (1994); to identify RNA ligands to reverse transcriptase, Chen & Gold, "Selection of High-Affinity RNA Ligands to Reverse Transcriptase: Inhibition of CDNA Synthesis and RNase H Activity," Biochemistry 33:8746–56 (1994); and to identify catalytic antibodies specific to a particular reaction transition state, Posner et al., "Catalytic Antibodies: Perusing Combinatorial Libraries," Trends. Biochem. Sci. 19:145–50 (1994).

The diversity of libraries generated using combinatorial strategies is impressive. For example, these methods have been used to generate a library containing four trillion decapeptides, Pinilla et al., "Investigation of Antigen-Antibody Interactions Using a Soluble, Non-Support-Bound Synthetic Decapeptide Library Composed of Four Trillion ($4\times10^{12}$) Sequences," Biochem. J. 301:847–53 (1994); 1,4-benzodiazepines libraries, Bunin et al., "The Combinatorial Synthesis and Chemical and Biological Evaluation of a 1,4-Benzodiazepine Library," Proc. Natl. Acad. Sci. 91:4708–12 (1994) and U.S. Pat. No. 5,288,514, entitled "Solid Phase and Combinatorial Synthesis of Benzodiazepine Compounds on a Solid Support," issued Feb. 22, 1994; libraries containing multiple small ligands tied together in the same molecules, Wallace et al., "A Multimeric Synthetic Peptide Combinatorial Library," Pent. Res. 7:27–31 (1994); libraries of small organics, Chen et al., "'Analogous' Organic Synthesis of Compound Libraries: Validation of Combinatorial Chemistry in Small-Molecule Synthesis," J. Am. Chem. Soc. 116:2661–2662 (1994); libraries of peptidosteroidal receptors, Boyce & Nestler, "Peptidosteroidal Receptors for Opioid Peptides: Sequence-Selective Binding Using a Synthetic Receptor Library," J. Am. Chem. Soc. 116:7955–7956 (1994); and peptide libraries containing non-natural amino acids, Kerr et al;, "Encoded Combinatorial Peptide Libraries Containing Non-Natural Amino Acids," J. Am. Chem. Soc. 115:2529–31 (1993).

To date, three general strategies for generating combinatorial libraries have emerged: "spatially-addressable," "split-bead" and recombinant strategies.

These methods differ in one or more of the following aspects: reaction vessel design, polymer type and composition, control of physical constants such as time, temperature and atmosphere, isolation of products, solid-phase or solution-phase methods of assay, simple or complex mixtures, and method for elucidating the structure of the individual library members.

Of these general strategies, several sub-strategies have been developed. One spatially-addressable strategy that has emerged involves the generation of peptide libraries on immobilized pins that fit the dimensions of standard microtitre plates. See PCT Publication Nos. 91/17271 and 91/19818, each of which is incorporated herein by reference. This method has been used to identify peptides which mimic discontinuous epitopes, Geysen et al., BioMed. Chem. Lett. 3:391–404 (1993), and to generate benzodiazepine libraries, U.S. Pat. No. 5,288,514, entitled "Solid Phase and Combinatorial Synthesis of Benzodiazepine Compounds on a Solid Support," issued Feb. 22, 1994 and Bunin et al., "The Combinatorial Synthesis and Chemical and Biological Evaluation of a 1,4-Benzodiazepine Library," Proc. Natl. Acad. Sci. 91:4708–12 (1994). The structures of the individual library members can be decoded by analyzing the pin location in conjunction with the sequence of reaction steps used during the synthesis.

A second, related spatially-addressable strategy that has emerged involves solid-phase synthesis of polymers in individual reaction vesels, where the individual vessels are arranged into a single reaction unit. An illustrative example of such a reaction unit is a standard 96-well microtitre plate; the entire plate comprises the reaction unit and each well corresponds to a single reaction vessel. This approach is an extrapolation of traditional single-column solid-phase synthesis.

As is exemplified by the 96-well plate reaction unit, each reaction vessel is spatially defined by a two-dimensional matrix. Thus, the structures of individual library members can be decoded by analyzing the sequence of reactions to which each well was subjected.

Another spatially-addressable strategy employs "tea bags" to hold the synthesis resin. The reaction sequence to which each tea bag is subject is recorded, which determines the structure of the oligomer synthesized in each tea bag. See for example, Lam et al., "A New Type of Synthetic Peptide Library for Identifying Ligand-Binding Activity," Nature 354:82–84 (1991); Houghten et al., "Generation and Use of Synthetic Peptide Combinatorial Libraries for Basic Research and Drug Discovery," Nature 354:84–86 (1991); Houghten, "General Method for the Rapid Solid-Phase Synthesis of Large Numbers of Peptides: Specificity of Antigen-Antibody Interaction at the Level of Individual Amino Acids," Proc. Natl. Acad. Sci. 82:5131–5135 (1985); and Jung et al., Agnew. Chem. Int. Ed. Engl. 91:367–383 (1992), each of which is incorporated herein by reference.

In another recent development, scientists combined the techniques of photolithography, chemistry and biology to create large collections of oligomers and other compounds on the surface of a substrate (this method is called "VLSIPS™"). See, for example, U.S. Pat. No. 5,143,854; PCT Publication No. 90/15070; PCT Publication No. 92/10092 entitled "Very Large Scale Immobilized Polymer Synthesis," Jun. 25, 1992; Fodor et al., "Light-Directed Spatially Addressable Parallel Chemical Synthesis," Science 251:767–773 (1991); Pease et al., "Light-Directed Oligonucleotide Arrays for Rapid DNA Sequence Analysis," Proc. Natl. Acad. Sci. 91:5022–5026 (1994); and Jacobs & Fodor, "Combinatorial Chemistry: Applications of Light-Directed Chemical Synthesis," Trends. Biotechnology 12(1): 19–26 (1994), each of which is incorporated herein by reference.

Others have developed recombinant methods for preparing collections of oligomers. See, for example, PCT Publication No. 91/17271; PCT Publication No. 91/19818; Scott, "Discovering Peptide Ligands Using Epitope Libraries," TIBS 17:241–245 (1992); Cwirla et al., "Peptides on Phage: A Vast Library of Peptides for Identifying Ligands," Proc. Natl. Acad. Sci. 87:6378–6382 (1990); Devlin et al., "Random Peptide Libraries: A Source of Specific Protein Binding Molecules," Science 249:404–406 (1990); and Scott & Smith, "Searching for Peptide Ligands with an Epitope Library," Science 249:386–390 (1990). Using these methods, one can identify each oligomer in the library by determining the coding sequences in the recombinant organism or phage. However, since the library members are generated in vivo, recombinant methods are limited to polymers whose synthesis is mediated in the cell. Thus, these methods typically have been restricted to constructing peptide libraries.

A third general strategy that has emerged involves the use of "split-bead" combinatorial synthesis strategies. See, for example, Furka et al., Int. J. Pept. Protein Res. 37:487–493 (1991), which is incorporated herein by reference. In this method synthesis supports are apportioned into aliquots, each aliquot exposed to a monomer, and the beads pooled. The beads are then mixed, reapportioned into aliquots, and exposed to a second monomer. The process is repeated until the desired library is generated.

Since the polymer libraries generated with the split-bead method are not spatially-addressable, the structures of the individual library members cannot be elucidated by analyzing the reaction histogram. Rather, structures must be determined by analyzing the polymers directly. Thus, one limitation of the split-bead approach is the requisite for an available means to analyze the polymer composition. While sequencing techniques are available for peptides and nucleic acids, sequencing reactions for polymers of other composition, such as for example carbohydrates, organics, peptide nucleic acids or mixed polymers may not be readily known.

Variations on the "split-bead" scheme have emerged that obviate the need to sequence the library member directly. These methods utilize chemicals to tag the growing polymers with a unique identification tag ("co-synthesis" strategies). See, for example, PCT Publication No. WO 94/08051 entitled "Complex Combinatorial Chemical Libraries Encoded with Tags," Apr. 14, 1994; Nestler et al., "A General Method for Molecular Tagging of Encoded Combinatorial Chemistry Libraries," J. Org. Chem. 59:4723–4724 (1994); PCT Publication No. WO 93/06121 entitled "Method of Synthesizing Diverse Collections of Oligomers," Apr. 1, 1993; Needels et al., Proc. Natl. Acad. Sci. 90:10700–10704 (1993); Kerr et al., "Encoded Combinatorial Peptide Libraries Containing Non-Natural Amino Acids," J. Amer. Chem. Soc. 115:2529–2531 (1993); and Brenner & Lerner, "Encoded Combinatorial Chemistry," Proc. Natl. Acad. Sci. 89:5381–5383 (1992), each of which is incorporated herein by reference.

Encoding library members with chemical tags occurs in such a fashion that unique identifiers of the chemical structures of the individual library members are constructed in parallel, or are co-synthesized, with the library members. Typically, in a linear three component synthesis containing building blocks A, B and C in the process of generating library member ABC, an encoding. tag is introduced, at each stage such that the tags $T_A$, $T_B$ and $T_C$ would encode for individual inputs in the library. The synthesis would proceed as follows: (a) Chemical A is coupled onto a synthesis bead, immediately followed by coupling tag $T_A$ to the bead; (b) The bead is subject to deprotection conditions which remove the protecting group selectively from A, leaving $T_A$ protected. Chemical B is coupled to the bead, generating the sequence AB. The bead is then subject to deprotection which selectively removes the protecting group from $T_A$, and $T_B$ is coupled to the bead, generating tag sequence $T_AT_B$; (c) The third component C and concomitant tag $T_C$ is added to the bead in the manner described above, generating library sequence ABC and tag sequence $T_AT_BT_C$.

For large libraries containing three chemical inputs, the chemical tagging sequence is the same. Thus, to generate a large library containing the complete set of three-input, one hundred unit length polymers, or $100^3=10^6$ library members, unique identifying tags are introduced such that there is a unique identifier tag for each different chemical structure. Theoretically, this method is applicable to libraries of any complexity as long as tagging sequences can be developed that have at least the same number of identification tags as there are numbers of unique chemical structures in the library.

While combinatorial synthesis strategies provide a powerful means for rapidly identifying target molecules, substantial problems remain. For example, since members of spatially addressable libraries must be synthesized in spatially segregated arrays, only relatively small libraries can be constructed. The position of each reaction vessel in a spatially addressable library is defined by an XY coordinate pair such that the entire library is defined by a two-dimensional matrix. As the size of the library increases the dimensions of the two-dimensional matrix increases. In addition, as the number of different transformation events used to construct the library increases linearly, the library size increases exponentially. Thus, while generating the complete set of linear tetramers comprised of four different inputs requires only a 16×16 matrix ($4^4$=256 library members), generating the complete set of linear octamers composed of four different inputs requires a 256×256 matrix ($4^8$=65,536 library members), and generating the complete set of linear tetramers composed of twenty different inputs requires a 400×400 matrix ($20^4$=160,000 library members). Therefore, not only does the physical size of the library matrix quickly become unwieldy (constructing the complete set of linear tetramers composed of twenty different inputs using spatially-addressable techniques requires 1667 microtitre plates), delivering reagents to each reaction vessel in the matrix requires either tedious, time-consuming manual manipulations, or complex, expensive automated equipment.

While the VLSIPS™ method attempts to overcome this limitation through miniaturization, VLSIPS™ requires specialized photoblocking chemistry, expensive, specialized synthesis equipment and expensive, specialized assay equipment. Thus, the VLSIPS™ method is not readily and economically adaptable to emerging solid phase chemistries and assay methodologies.

Split bead methods also suffer severe limitations. Although large libraries can theoretically be constructed using split-bead methods, the identity of library members displaying a desirable property must be determined by analytical chemistry. Accordingly, split-bead methods can only be employed to synthesize compounds that can be readily elucidated by microscale sequencing, such as polypeptides and polynucleotides.

Co-synthesis strategies have attempted to solve this structure elucidation problem. However, these methods also suffer limitations. For example, the tagging structures may be incompatible with synthetic organic chemistry reagents and conditions. Additional limitations follow from the necessity for compatible protecting groups which allow the alternating co-synthesis of tag and library member, and assay confusion that may arise from the tags selectively binding to the assay receptor.

Finally, since methods such as the preceding typically require the addition of like moieties, there is substantial interest in discovering methods for producing labeled libraries of compounds which are not limited to sequential addition of like moieties, and which are amenable to any chemistries now known or that will be later developed to generate chemical libraries. Such methods would find application, for example, in the modification of steroids, sugars, co-enzymes, enzyme inhibitors, ligands and the like, which frequently involve a multi-stage synthesis in which one would wish to vary the reagents and/or conditions to provide a variety of compounds.

In such methods the reagents may be organic or inorganic reagents, where functionalities or side groups may be introduced, removed or modified, rings opened or closed, stereochemistry changed, and the like.

From the above, one can recognize that there is substantial interest in developing improved methods and apparatus for the synthesis of complex labeled combinatorial chemical libraries which readily permit the construction of libraries of virtually any composition and which readily permit accurate structural determination of individual compounds within the library that are identified as being of interest. Many of the disadvantages of the previously-described methods as well as many of the needs not met by them are addressed by the present invention, which as described more fully hereinafter, provides myriad advantages over these previously-described methods.

Glossary

The following terms are intended to have the following general meanings as they are used herein:

Labeled Synthetic Oligomer Library: A "labeled synthetic oligomer library" is a collection of random synthetic oligomers wherein each member of such a library is labeled with a unique identifier tag from which the structure or sequence of each oligomer can be deduced.

Identifier Tag: An "identifier tag" is any detectable attribute that provides a means whereby one can elucidate the structure of an individual oligomer in a labeled synthetic oligomer library. Thus, an identifier tag identifies which transformation events an individual oligomer has experienced in the synthesis of a labeled synthetic oligomer library, and at which reaction cycle in a series of synthesis cycles each transformation event was experienced.

An identifier tag may be any detectable feature, including, for example: a differential absorbance or emission of light; magnetic or electronically pre-encoded information; or any other distinctive mark with the required information. An identifier tag may be pre-encoded with unique identifier information prior to synthesis of a labeled synthetic oligomer library, or may be encoded with a identifier information in concomitant with synthesis of a labeled synthetic oligomer library.

In this latter embodiment, the identifier information added at each synthesis cycle is preferably added in a sequential fashion, such as, for example digital information, with the identifier information identifying the transformation event of synthesis cycle two being appended onto the identifier information identifying the transformation event of synthesis cycle one, and so forth.

Preferably, an identifier tag is impervious to the reaction conditions used to construct the labeled synthetic oligomer library.

A preferred example of an identifier tag is a microchip that is pre-encoded or encodable with information, which information is related back to a detector when the microchip is pulsed with electromagnetic radiation.

Pre-Encoded Identifier Tag: A "pre-encoded identifier tag" is an identifier tag that is pre-encoded with unique identifier information prior to synthesis of a labeled synthetic oligomer library. A preferred example of such a pre-encoded identifier tag is a microchip that is pre-encoded with information, which information is related back to a detector when the microchip is pulsed with electromagnetic radiation.

Encodable Identifier Tag: An "encodable identifier tag" is an identifier tag that is capable of receiving identifier information from time to time. An encodable identifier tag may or may not be pre-encoded with partial or complete identifier information prior to synthesis of a labeled synthetic oligomer library. A preferred example of such an encodable identifier tag is a microchip that is capable of receiving and storing information from time to time, which information is related back to a detector when the microchip is pulsed with electromagnetic radiation.

Transformation Event: As used herein, a "transformation event" is any event that results in a change of chemical structure of an oligomer or polymer. A "transformation event" may be mediated by physical, chemical, enzymatic, biologicall or other means, or a combination of means, including but not limited to, photo, chemical, enzymatic or biologically mediated isomerization or cleavage; photo, chemical, enzymatic or biologically mediated side group or functional group addition, removal or modification; changes in temperature; changes in pressure; and the like. Thus, "transformation event" includes, but is not limited to, events that result in an increase in molecular weight of an oligomer or polymer, such as, for example, addition of one or a plurality of monomers, addition of solvent or gas, or coordination of metal or other inorganic substrates such as, for example, zeolites; events that result in a decrease in molecular weight of an oligomer or polymer, such as, for example, de-hydrogenation of an alcohol to from an alkene or enzymatic hydrolysis of an ester or amide; events that result in no net change in molecular weight of an oligomer or polymer, such as, for example, stereochemistry changes at one or a plurality of a chiral centers, Claissen rearrangement, or Cope rearrangement; and other events as will become apparent to those skilled in the art upon review of this disclosure. See, for example, application Ser. No. 08/180,863 filed Jan. 13, 1994, which is assigned to the assignee of the present invention and PCT Publication WO 94/08051 entitled "Complex Combinatorial Libraries Encoded with Tags," Apr. 14 (1994), each of which is incorporated herein by reference.

Monomer: As used herein, a "monomer" is any atom or molecule capable of forming at least one chemical bond. Thus, a "monomer" is any member of the set of atoms or molecules that can be joined together as single units in a multiple of sequential or concerted chemical or enzymatic reaction steps to form an oligomer or polymer. Monomers may have one or a plurality of functional groups, which functional groups may be, but need not be, identical.

The set of monomers useful in the present invention includes, but is not restricted to, alkyl and aryl amines; alkyl and aryl mercaptans; alkyl and aryl ketones; alkyl and aryl carboxylic acids; alkyl and aryl ester; alkyl and aryl ethers; alkyl and aryl sulfoxides; alkyl and aryl sulfones; alkyl and aryl sulfonamides; phenols; alkyl alcohols; alkyl and aryl alkenes; alkyl and aryl lactams; alkyl and aryl lactones; alkyl and aryl di- and polyenes; alkyl and aryl alkynes; alkyl and aryl unsaturated ketones; aldehydes; sulfoxides; sulfones; heteroatomic compounds containing one or more of the atoms of: nitrogen, sulfur, phosphorous, oxygen, and other polyfunctional molecules containing one or more of the above functional groups; L-amino acids; D-amino acids; deoxyribonucleosides; deoxyribonucleotides; ribonucleosides; ribonucleotides; sugars; benzodiazenines; β-lactams; hydantoins; quinones; hydroquinones; terpenes; and the like.

The monomers of the present invention may have groups protecting the functional groups within the monomer. Suitable protecting groups will depend on the functionality and particular chemistry used to construct the library. Examples of suitable functional protecting groups will be readily apparent to skilled artisans, and are described, for example, in Greene and Wutz, Protecting Groups in Organic Synthesis, 2d ed., John Wiley & Sons, NY (1991), which is incorporated herein by reference.

As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer.

Oligomer or Polymer: As used herein, an "oligomer" or "polymer" is any chemical structure that can be synthesized using the combinatorial library methods of this invention, including, for example, amides, esters, thioethers, ketones, ethers, sulfoxides, sulfonamides, sulfones, phosphates, alcohols, aldehydes, alkenes, alkynes, aromatics, polyaromatics, heterocyclic compounds containing one or more of the atoms of: nitrogen, sulfur, oxygen, and phosphorous, and the like; chemical entities having a common core structure such as, for example, terpenes, steroids, β-lactams, benzodiazepines, xanthates, indoles, indolones, lactones, lactams, hydantoins, quinones, hydroquinones, and the like; chains of repeating monomer units such as polysaccharides, phospholipids, polyurethanes, polyesters, polycarbonates, poly ureas, polyamides, polyethyleneimines, poly arylene sulfides, polyimides, polyacetates, polypeptides, polynucleotides, and the like; or other oligomers or polymers as will be readily apparent to one skilled in the art upon review of this disclosure. Thus, an "oligomer" and "polymer" of the present invention may be linear, branched, cyclic, or assume various other forms as will be apparent to those skilled in the art.

Concerted: As used herein "concerted" means synchronous and asynchronous formation of one or more chemical bonds in a single reaction step.

Substrate: As used herein, a "substrate" is a synthesis means linked to an identifier tag. By way of example and not limitation, a "substrate" may be an identifier tag functionalized with one or a plurality of groups or linkers suitable for synthesis; a glass or polymer encased identifier tag, which glass or polymer is functionalized with one or a plurality of groups or linkers suitable for synthesis; an identifier tag that is coated with one or a plurality of synthesis supports; an identifier tag retained within a frame or housing, which frame or housing is functionalized with one or a plurality of groups or linkers suitable for synthesis; an identifier tag retained within a frame or housing, which frame or housing also retains one or a plurality of synthesis supports; and the like.

Synthesis Means: A "synthetic means" is any means for carrying out synthesis of a labeled synthetic oligomer library. Thus, "synthesis means" may comprise reaction vessels, columns, capillaries, frames, housings, and the like, suitable for carrying out synthesis reactions; one or a plurality of synthesis supports suitable for carrying out synthesis reactions; or functional groups or linkers attached to an identifier tag suitable for carrying out synthesis reactions.

"Synthesis means" may be constructed such they are capable of retaining identifier tags and/or synthesis supports.

In a preferred embodiment a "synthesis means" is one or a plurality of synthesis supports.

Synthesis Support: A "synthesis support" is a material having a rigid or semi-rigid surface and having functional groups or linkers, or that is capable of being derivatized with functional groups or linkers, that are suitable for carrying out synthesis reactions.

Such materials will preferably take the form of small beads, pellets, disks, capillaries, hollow fibers, needles, solid fibers, cellulose beads, pore-glass beads, silica gels, polystyrene beads optionally cross-linked with polyethylene glycol divinylbenzene, grafted co-poly beads, polyacrylamide beads, latex beads, dimethylacrylamide beads optionally cross-linked with N,N'-bis-acryloyl ethylene diamine, glass particles coated with a hydrophobic polymer, or other convenient forms.

"Synthesis supports" may be constructed such that they are capable of retaining identifier tags.

Linker: A "linker" is a moiety, molecule, or group of molecules attached to a synthesis support or substrate and spacing a synthesized polymer or oligomer from the synthesis support or substrate. A "linker" can also be a moiety, molecule, or group of molecules attached to a substrate and spacing a synthesis support from the substrate.

Typically a linker will be bi-functional, wherein said linker has a functional group at one end capable of attaching to a monomer, oligomer, synthesis support or substrate, a series of spacer residues, and a functional group at another end capable of attaching to a monomer, oligomer, synthesis support or substrate. The functional groups may be, but need not be, identical.

Spacer residues: "Spacer residues" are atoms or molecules positioned between the functional groups of a bifunctional linker, or between a functional group of a linker and the moiety to which the linker is attached. "Spacer residues" may be atoms capable of forming at least two covalent bonds such as carbon, silicon, oxygen, sulfur, phosphorous, and the like, or may be molecules capable of forming at least two covalent bonds such as amino acids, peptides, nucleosides, nucleotides, sugars, carbohydrates, aromatic rings, hydrocarbon rings, linear and branched hydrocarbons, and the like.

Linked together the spacer residues may be rigid, semi-rigid or flexible. Linked spacer residues may be, but need not be, identical.

Pre-encoded Substrate: A "pre-encoded substrate" is a substrate wherein the identifier tag is a pre-encoded identifier tag.

Encodable Substrate: An "encodable substrate" is a substrate wherein the identifier tag is an encodable identifier tag.

Synthetic: A compound is "synthetic" when produced by in vitro chemical or enzymatic synthesis.

Oligomer or Polymer Sequence: As used herein "oligomer sequence" or "polymer sequence" refers to the chemical structure of an oligomer or polymer.

SUMMARY OF THE INVENTION

The present invention relates to labeled libraries of random oligomers. Each library member is labeled with a unique identifier tag from which the structure of the library member can be readily ascertained.

The present invention also relates to methods and apparatus for synthesizing labeled libraries of random oligomers. The random oligomers are generally synthesized on synthesis supports, but may be cleaved from these supports or synthesized in solution phase to provide a soluble library. In a preferred embodiment the oligomers are composed of a set of monomers, the monomers being any number of the set of atoms or molecules that can be joined together to form an oligomer or polymer. The library is then screened to isolate individual oligomers that bind to a receptor or possess some desired property. In a preferred embodiment, each oligomer structure in the library is unique.

The identifier tag is used to identify the structures of oligomers contained in the labeled synthetic oligomer library. The identifier tag, which may be linked to the oligomer in a variety of fashions, may be any detectable feature that in some way carries the required information, and that is decipherable. Preferably, the identifier tag is impervious to the chemical reagents used to synthesize the library.

In a preferred embodiment the identifier tag relates a signal to a detector upon excitation with electromagnetic radiation. Suitable identifier tags may be, by way of example and not limitation, bar codes that can be scanned with a laser, chemical moieties that differentially emit or absorb light, such as chromophores, fluorescent, and phosphorescent moieties, or microchips that are pre-encoded or are encodable with a unique radiofrequency "fingerprint" that emit a detectable signal when pulsed with electromagnetic radiation.

In a further preferred embodiment the identification tags are encased in glass or a polymeric material that can be coated with synthesis supports or derivatized with functional groups or linkers suitable for synthesis. Preferably, the identifier tags can be sorted with automatic sorting equipment. Such polymeric materials and sorting equipment are widely known in the art.

DETAILED DESCRIPTION OF THE INVENTION

The present invention provides labeled synthetic libraries of random oligomers and methods and apparatus for generating labeled synthetic oligomer libraries. Each member of such a library is labeled with a unique identifier tag that specifies the structure or sequence of the oligomer. In a preferred embodiment of the present invention the identifier tag is a microchip that is pre-encoded or encodable with information that is related back to a detector when the identifier tag is pulsed with electromagnetic radiation.

I. Labeled Oligomer Libraries

The present invention relates to labeled libraries of random oligomers. Each member of a random oligomer library is linked to an identifier tag such that the structure of the oligomer library member can be readily ascertained. The random oligomer library generally comprises a highly diverse collection of oligomers, wherein each member of such library comprises a single oligomer structure (e.g., a benzodiazepine). The oligomers may be soluble or may be bound to a synthesis support or substrate.

Figure 7:
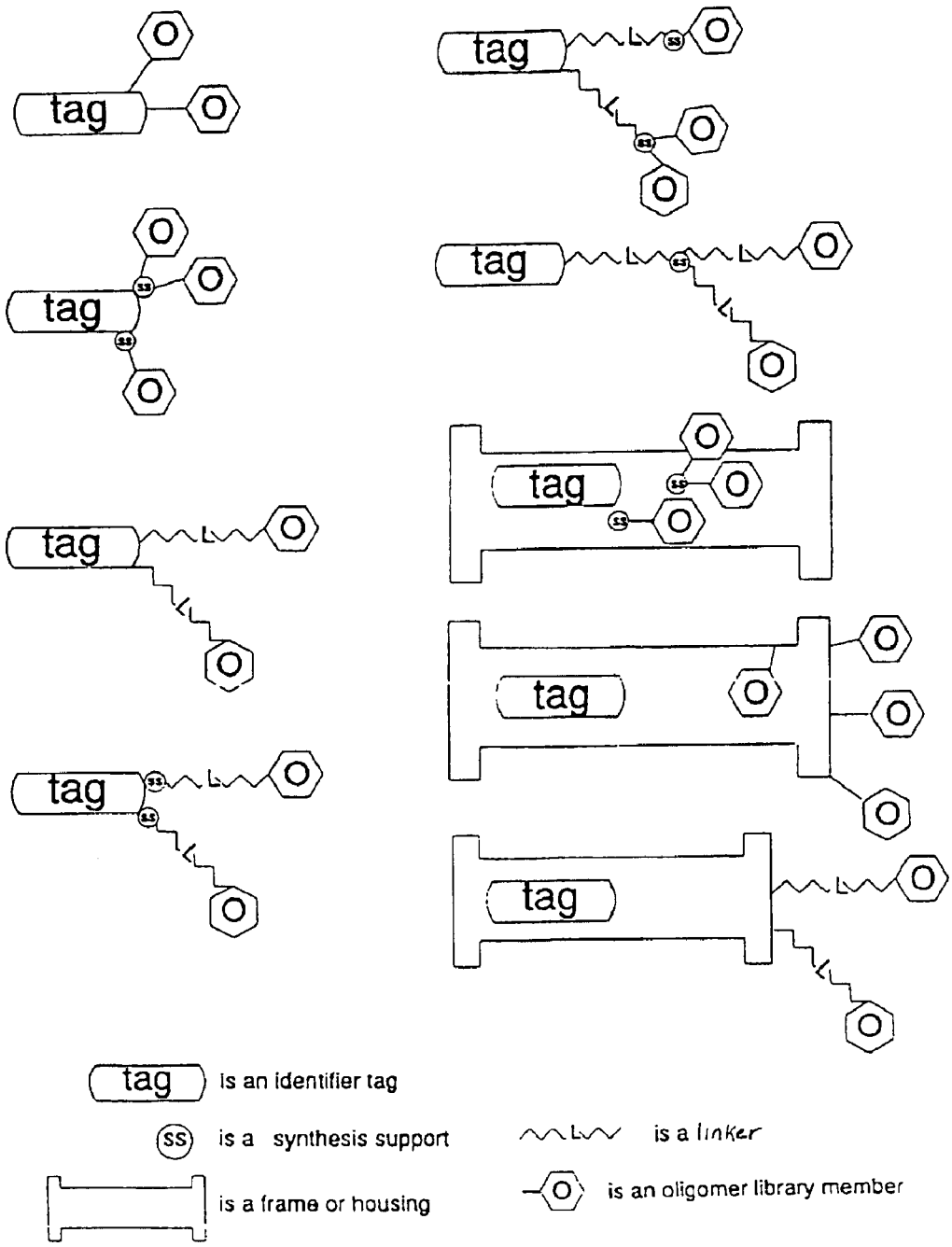
FIG. 7 schematically illustrates several ways in which an identifier tag can be linked to an oligomer library member.

The library members may be linked to an identifier tag in a variety of fashions. See, for example, FIG. 7. For example, an oligomer library member may be attached to a synthesis support, which synthesis support is retained within a reaction vessel, frame or housing that also retains an identifier tag. As another example, a library member may be attached to a synthesis support which is in turn attached to an identifier tag. The library member may be attached directly to a functional group on the synthesis support, but will usually be attached by means of a linker. The linker will generally be a bi-functional linker, which bi-functional linker comprises a functional group capable of attaching to a monomer, oligomer, synthesis support or substrate on one end, a series of spacer residues, and a functional group capable of attaching to a monomer, oligomer or synthesis support or substrate at another end.

Attachment of a synthesis support to an identifier tag can be mediated by a variety of means. For example, an identifier tag may be coated with one or a plurality of synthesis supports, which synthesis supports are attached to the identifier tag by physical means such as glue or magnetic attraction. In one embodiment a synthesis support may be a polymer capable of being functionalized with reactive groups or linkers, which synthesis support is molded into a frame or housing that retains an identifier tag.

Alternatively, one or a plurality of synthesis supports may be covalently attached to an identifier tag. Covalent attachment may be directly to a functional group on the identifier tag, or may be mediated by a linker as described above.

In another embodiment, a library member may be attached directly to a functional group on an identifier tag, or to a linker which is attached to a functional group on an identifier tag.

Synthesis supports and substrates may have a plurality of functional groups or linkers, such that each synthesis support or substrate may have a plurality of oligomer library members of identical sequence attached thereto. The quantity synthesized of each library member comprising the labeled oligomer library can be varied by varying the number of synthesis supports, functional groups or linkers on synthesis supports, or functional groups or linkers on substrates. Thus, the labeled oligomer library of the present invention may comprise milligram quantities of each library member structure, thereby providing a sufficient quantity of each library member for multiple assays or other analytical experiments.

The labeled oligomer libraries of the present invention generally comprise a highly diverse collection of oligomers. Such a library may contain, for example, all $N^X$ different oligomers, wherein each oligomer is synthesized in a series of X synthesis cycles using N different transformation events. As a specific example, a library may contain all combinations of $N^X$ different oligomers; which oligomers are composed of N different monomers assembled in X synthesis cycles.

The library may also contain oligomers having been synthesized with different transformation events at, for example, only one or a small number of cycles in the synthesis series, while having identical transformation events at all other cycles. As a specific example, a library may contain oligomers having different monomers at only one or a small number of positions while having identical monomers at all other positions.

Oligomers or polymers of the present invention are formed from a stepwise or concerted series of transformation events. A transformation event is any event that results in a change of chemical structure of an oligomer or polymer. A transformation event may be mediated by physical, chemical, enzymatic, biological or other means, or a combination of means, including but not limited to, photo, chemical, enzymatic or biologically mediated isomerization or cleavage; photo, chemical, enzymatic or biologically mediated side is group or functional group addition, removal or modification; changes in temperature; changes in pressure; and the like. Thus, transformation events include, but are not limited to, events that result in an increase in molecular weight of an oligomer or polymer, such as, for example, addition of one or a plurality of monomers, addition of solvent or gas, or coordination of metal or other inorganic substrates such as, for example zeolites; events that result in a decrease in molecular weight of an oligomer or polymer, such as, for example, dehydrogenation of an alcohol to from an alkene, or enzymatic hydrolysis of an ester or amide; events that result in no net change in molecular weight of an oligomer or polymer, such as, for example, stereochemistry changes at one or a plurality of a chiral centers, Claissen rearrangement, or Cope rearrangement; and other events as will become apparent to those skilled in the art upon review of this disclosure. See, for example, application Ser. No. 08/180,863 filed Jan. 13, 1994, which is assigned to the assignee of the present invention and PCT Publication WO 94/08051 entitled "Complex Combinatorial Libraries Encoded with Tags," Apr. 14 (1994), each of which is incorporated herein by reference.

In a preferred embodiment, at lease one transformation event in the generation of a labeled synthetic oligomer library is the stepwise or concerted enzymatic or chemical addition of one or a plurality of monomers.

In another preferred embodiment, each transformation event in the generation of a labeled synthetic oligomer library is the stepwise or concerted enzymatic or chemical addition of one or a plurality of monomers.

A monomer is any atom or molecule capable of forming at least one chemical bond. Thus, a monomer is any member of the set of atoms or molecules that can be joined together as single units in a multiple of sequential or concerted chemical or enzymatic reaction steps to form an oligomer or polymer. The set of monomers useful in the present invention includes, but is not retricted to, alkyl and aryl amines; alkyl and aryl mercaptans; alkyl and aryl ketones; alkyl and aryl carboxylic acids; alkyl and aryl esters; alkyl and aryl ethers; alkyl and aryl sulfoxides; alkyl and aryl sulfones; alkyl and aryl sulfonamides; phenols; alkyl alcohols; alkyl and aryl alkenes; alkyl and aryl lactams; alkyl and aryl lactones; alkyl and aryl di- and polyenes; alkyl and aryl alkynes; alkyl and aryl unsaturated ketones; aldehydes; sulfoxides; sulfones; heteroatomic compounds containing one or more of the atoms of: nitrogen, sulfur, phosphorous, oxygen, and other polyfunctional molecules containing one or more of the above functional groups; L-amino acids; D-amino acids; deoxyribonucleosides; deoxyribonucleotides; ribonucleosides; ribonucleotides; sugars; benzodiazepines; β-lactams; hydantoins; quinones; hydroquinones; terpenes; and the like.

The monomers of the present invention may have groups protecting the functional groups within the monomer. Suitable protecting groups will depend on the functionality and particular chemistry used to construct the library. Examples of suitable functional protecting groups will be readily apparent to skilled artisans, and are described, for example, in Greene and Wutz, Protecting Groups in Organic Synthesis, 2d ed., John Wiley & Sons, NY (1991), which is incorporated herein by reference.

As used herein, monomer refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. Thus, as the skilled artisan will appreciate, the oligomer or polymer library members generated by practicing the present invention may serve as monomers in a the synthesis of a labeled synthetic oligomer libraries.

Accordingly, oligomers or polymers of the present invention comprise any chemical structure that can be synthesized using the combinatorial library methods of this invention, including, for example, amides, esters, thioethers, ketones, ethers, sulfoxides, sulfonamides, sulfones, phosphates, alcohols, aldehydes, alkenes, alkynes, aromatics, polyaromatics, heterocyclic compounds containing one or more of the atoms of: nitrogen, sulfur, oxygen, and phosphorous, and the like; chemical entities having a common core structure such as, for example, terpenes, steroids, β-lactams, benzodiazepines, xanthates, indoles, indolones, lactones, lactams, hydantoins, quinones, hydroquinones, and the like; chains of repeating monomer units such as polysaccharides, phospholipids, polyurethanes, polyesters, polycarbonates, poly ureas, polyamides, polyethyleneimines, poly arylene sulfides, polyimides, polyacetates, polypeptides, polynucleotides, and the like; or other oligomers or polymers as will be readily apparent to one skilled in the art upon review of this disclosure. Thus, an "oligomer" and "polymer" of the present invention may be linear, branched, cyclic, or assume various other forms as will be apparent to those skilled in the art.

A labeled oligomer library of the present invention may comprise virtually any level of complexity and is limited in size only by the physical size of a substrate. An oligomer library will typically comprise from about 10 to about 5000 library members, preferably from about 1000 to about 250,000 library members, and more preferably from about 50,000 to about $10^6$ library members.

The labeled synthetic oligomer libraries of the present invention have a wide variety of uses. By way of example and not limitation, labeled synthetic oligomer libraries can be used to identify peptide, nucleic acid, carbohydrate and/or other structures that bind to proteins, enzymes, antibodies, receptors and the like; identify sequence-specific binding drugs; identify epitopes recognized by antibodies; evaluate a variety of drugs for clinical diagnostic applications; identify materials that exhibit specific properties, such as, for example, ceramics; identify elements comprising superconducting compositions; combinations of the above; and other uses that will be apparent to those skilled in the art.

II. Methods for Generating Labeled Oligomer Libraries

The present invention also provides methods and apparatus for generating labeled oligomer libraries. The general methods typically involve synthesizing the oligomers in a random combinatorial fashion by a stepwise or concerted series of transformation events. A labeled oligomer library may be produced by synthesizing on each of a plurality of identifier tags linked to a synthesis means ("substrates") a single oligomer structure, the oligomer structure being different for different substrates.

Substrates used for practicing the methods of the present invention include, but are not limited to, an identifier tag functionalized with one or a plurality of groups or linkers suitable for synthesis; a glass or polymer encased identifier tag, which glass or polymer is functionalized with one or a plurality of groups or linkers suitable for synthesis; an identifier tag that is coated with one or a plurality of synthesis supports; an identifier tag retained within a frame or housing, which frame or housing is functionalized with one or a plurality of groups or linkers suitable for synthesis; an identifier tag retained within a frame or housing, which frame or housing also retains one or a plurality of plurality of synthesis supports; and the like.

In a preferred embodiment a substrate comprises an identifier tag retained within a frame or housing, which frame or housing also retains one or a plurality of synthesis supports.

In another preferred embodiment a substrate comprises an identifier tag retained within a frame or housing, which frame or housing is functionalized with one or a plurality of groups or linkers suitable for synthesis.

In yet another preferred embodiment a substrate comprises an identifier tag, optionally encased in a glass or polymeric coating, which identifier tag is functionalized with one or a plurality of groups or linkers suitable for synthesis.

In one embodiment of the methods of the present invention a labeled synthetic oligomer library is generated that employs "birth-to-death" identifier tags. A "birth-to-death" identifier tag is a tag whose information content does not change during the course of synthesis. A labeled synthetic oligomer library is synthesized in a process comprising the steps of: (a) apportioning a plurality of substrates, each of which is pre-encoded with a unique identifier tag ("pre-encoded substrates") among a plurality of reaction vessels; (b) exposing the pre-encoded substrates in each reaction vessel to a one or a plurality of transformation events; (c) detecting and recording the identifier tag information from each pre-encoded substrate in each reaction vessel; (d) apportioning the pre-encoded substrates among a plurality of reaction vessels; and (e) repeating steps (a) through (c) from at least one to about twenty times.

A capping step wherein unreacted functional groups following a transformation event are "capped" with a highly reactive chemical moiety specific for the functional group(s) desired to be capped may be used after each transformation event. Suitable chemical capping moieties are well known in the art.

Typically, substantially equal numbers of substrates will be apportioned into each reaction vessel. The substrates may be apportioned in a stochastic manner at each step, but preferably will be apportioned in a non-stochastic fashion.

In a preferred embodiment, at least one transformation event is the stepwise or concerted chemical or enzymatic addition of one or a plurality of monomer units.

In an even more preferred embodiment, each transformation event is the stepwise or concerted chemical or enzymatic addition of one or a plurality of monomer units. For this preferred embodiment, a labeled synthetic oligomer library is synthesized in a process comprising the steps of: (a) apportioning a plurality of pre-encoded substrates among a plurality of reaction vessels; (b) exposing the pre-encoded substrates in each reaction vessel to a one or a plurality of monomer units; (c) detecting and recording the identifier tag information from each pre-encoded substrate in each reaction vessel; (d) apportioning the pre-encoded substrates among a plurality of reaction vessels; and (e) repeating steps (a) through (c) from at least one to about twenty times.

A capping step wherein unreacted functional groups following addition of one or a plurality of monomers are "capped" with a highly reactive chemical moiety specific for the functional group(s) desired to be capped may be used after each reaction cycle. Suitable chemical capping moieties are well known in the art.

As a specific example of the method, one may consider the synthesis of the set of linear oligomers three monomer residues in length, assembled from a set of four monomers A, B, C, D. See FIG. 1. The first monomer is coupled to four different aliquots of pre-encoded substrates, each different monomer in a different aliquot. The identifier information from each pre-encoded substrate is detected and recorded for each different aliquot. The pre-encoded substrates from all the aliquots are then redistributed for a second round of monomer addition.

The pre-encoded substrates may be redistributed in a stochastic fashion. For this method the pre-encoded substrates from all the aliquots are be pooled, which pool now contains approximately equal numbers of four different types of pre-encoded substrates, each of which is characterized by the monomer in the first residue position, and redistributed into the separate monomer reaction vessels containing A, B, C or D as the monomer. Alternatively, the pre-encoded substrates may be sorted and redistributed in a non-stochastic fashion into the separate monomer reaction vessels containing A, B, C or D as the monomer.

Following re-distribution a second monomer is coupled and the identifier information from each pre-encoded substrate again detected and recorded for each substrate in each reaction vessel. Each vessel now has substrates with four different monomers in position one and the monomer contained in each particular second reaction vessel in position two. The pre-encoded substrates from all reaction vessels are again redistributed among each of the four reaction vessels, and the coupling, detecting and recording process repeated. The process of sequential coupling and apportioning yields pre-encoded substrates that have passed through all the possible reaction pathways, and the collection of pre-encoded substrates displays all possible trimers composed of the four monomer inputs A, B, C and D ($4^3$=64 trimers).

The sequential detection and recording steps have provided a detailed list of the stepwise monomer additions to which each pre-encoded substrate was subjected ("reaction histogram"). For example, if the trimer sequence ABC was synthesized on a pre-encoded substrate bearing identifier tag signal "001", the recorded reaction histogram would reveal that in the first reaction step substrate 001 was contained in the reaction vessel containing monomer A, in the second reaction step substrate 001 was contained in the reaction vessel containing monomer B, and in the third step in the vessel containing monomer C. Thus, determining in which reaction vessel a particular pre-encoded substrate was contained at each reaction step reveals the polymer structure or sequence synthesized on the particular pre-encoded substrate. Thus, it can be appreciated that the number of unique identifier tags needed to label the library is dictated by the number of members in the library being generated.

In another embodiment of the present invention the identifier tags are encoded with information in parallel with generating the oligomer library ("encodable substrates"). The encodable substrates may be pre-encoded with partial identifier information prior to synthesis or may be blank. A labeled synthetic oligomer library is synthesized in a process comprising the steps of: (a) apportioning a plurality of encodable substrates among a plurality of reaction vessels; (b) exposing the substrates in each reaction vessel to one or a plurality of transformation events; (c) adding identifier information to each identifier tag in each reaction vessel; (d) apportioning the encodable substrates among a plurality of reaction vessels; and (e) repeating steps (a) through (c) from at least one to about twenty times.

A capping step wherein unreacted functional groups following a transformation event are "capped" with a highly reactive chemical moiety specific for the functional group(s) desired to be capped may be used after each transformation event. Suitable chemical capping moieties are well known in the art.

In a preferred embodiment, at least one transformation event is the stepwise or concerted chemical or enzymatic addition of one or a plurality of monomer units.

In an even more preferred embodiment, each transformation event is the stepwise or concerted chemical or enzymatic addition of one or a plurality of monomer units. For this preferred embodiment, a labeled synthetic oligomer library is synthesized in a process comprising the steps of: (a) apportioning a plurality of encodable substrates among a plurality of reaction vessels; (b) exposing the substrates in each reaction vessel to one or a plurality of units; (c) adding identifier information to each identifier tag in each reaction vessel; (d) apportioning the encodable substrates among a plurality of reaction vessels; and (e) repeating steps (a) through (c) from at least one to about twenty times.

A capping step wherein unreacted functional groups following addition of one or a plurality of monomer units are "capped" with a highly reactive chemical moiety specific for the functional group(s) desired to be capped may be used after each reaction cycle. Suitable chemical capping moieties are well known in the art.

Typically, substantially equal numbers of substrates will be apportioned into each reaction vessel. As discussed above, the redistribution process may be stochastic, but is preferably non-stochastic.

As a specific example of the method, one may again consider the synthesis of the set of oligomers three residues in length, assembled from a set of monomers A, B, C, D. See FIG. 2. The first monomer is coupled to four different aliquots of encodable substrates, each different monomer in a different aliquot. Identifier information is added to the identifier tags in each aliquot, with the identifier information being unique for each aliquot. Thus, each encodable substrate is characterized by the identity of the monomer in the first residue position. The encodable substrates are then redistributed among the separate monomer reaction vessels containing A, B, C, or D as the monomer.

The second residue is coupled and identifier information unique to each aliquot added to the encodable substrates in each reaction vessel. Following this reaction, each vessel now has encodable substrates with four different monomers in position one and the monomer contained in each particular second reaction vessel in position two. The encodable substrates from all reaction vessels are again redistributed among each of the four reaction vessels, the third monomer coupled and identifier information added. The process of sequential re-distributing and coupling yields substrates that have passed through all the possible reaction pathways, and the collection of substrates displays all possible trimers composed of the A, B, C, and D ($4^3$=64 trimers).

Each identifier tag is now labeled with sequential information that identifies the monomers to which each encodable substrate was exposed. For example, if one assigned the four monomers A, B, C and D identification labels according to a binary code such that A=00, B=01, C=10 and D=11, the encodable substrate containing the sequence ABC will contain an identifier tag that reads 000110.

It will be appreciated that the identifier tag "grows" with the growing oligomer, and thus the number of unique identification labels, which identification labels uniquely identify particular transformation events, is dictated by the number of transformation events used to generate the oligomer library. Accordingly, a unique identifier tag is generated for each oligomer in the library by the sequential addition of identification labels identifying the transformation events used to construct the library member.

As will be readily appreciated by those skilled in the art, the method of assembling oligomers from a stepwise or concerted series of transformation events can utilize any chemical, physical, enzymatic or biological means, or combinations thereof, that can effect a change in the structure of an oligomer or polymer. The oligomers can be synthesized by introducing, modifying, or removing functional groups or side chains, opening and/or closing rings, changing stereo chemistry, and the like. Accordingly, the resulting oligomers can be linear, branched, cyclic, or assume various other conformations that will be apparent to those of ordinary skill in the art. See FIGS. 3, 4, 5 and 6.

In addition, because the substrates are apportioned amongst a number of reaction vessels, transformation events using different physical chemical, enzymatic or biological chemistries, or combination thereof can be used to assemble the oligomers. Examples of the plethora of transformation events that can be used with the present invention are described in, for example, application Ser. No. 08/180,863 filed Jan. 13, 1994, which is assigned to the assignee of the present invention and PCT Publication WO 94/08057 entitled, "Complex Combinatorial Libraries Encoded with Tags" Apr. 14 (1994), each of which is incorporated herein by reference.

Thus, those skilled in the art will appreciate that the methods of the present invention can be used to synthesize labeled libraries of virtually any chemical composition including, but not limited to, amides, esters, thioethers, ketones, ethers, sulfoxides, sulfonamides, sulfones, phosphates, alcohols, aldehydes, alkenes, alkynes, aromatics, polyaromatics, heterocyclic compounds containing one or more of the atoms of: nitrogen, sulfur, oxygen, and phosphorous, and the like; chemical entities having a common core structure such as, for example, terpenes, steroids, β-lactams, benzodiazepines, xanthates, indoles, indolones, lactones, lactams, hydantoins, quinones, hydroquinones, and the like; chains of repeating monomer units such as polysaccharides, phospholipids, polyurethanes, polyesters, polycarbonates, poly ureas, polyamides, polyethyleneimines, poly arylene sulfides, polyimides, polyacetates, polypeptides, polynucleotides, and the like; or other oligomers or polymers as will be readily apparent to those skilled in the art.

In a preferred embodiment, at least one transformation event in the generation of a labeled synthetic oligomer library is the stepwise or concerted enzymatic or chemical addition of one or a plurality of monomers.

In another preferred embodiment, each transformation event in the generation of a labeled synthetic oligomer library is the stepwise or concerted enzymatic or chemical addition of one or a plurality of monomers.

In these preferred modes, the functionalities connecting monomers need not be identical. Thus, polymers composed of non-identical interlinkages are contemplated by the preferred embodiments. Also contemplated are oligomers that are composed of non-uniform monomer composition. As one example, an oligomer may be composed of aryl or alkyl hydroxyl, aryl or alkyl carboxylic acid, and aryl or alkyl amine monomers. As another example, an oligomer may be composed of deoxyribonucleoside, carbohydrate, and amino acid monomer units.

Although typically the present invention will utilize solid phase synthesis strategies, the present invention also contemplates solution phase chemistries. Techniques for solid phase synthesis of peptides are described, for example, in Atherton and Sheppard, Solid Phase Peptide Synthesis: A Practical Approach, IRL Press at Oxford University Press, Oxford, England (1989); for oligonucleotides in, for example, Gait, Oligonucleotide Synthesis: A Practical Approach, IRL Press at Oxford University Press, Oxford, England (1984); each of which is incorporated herein by reference.

Techniques for solution and solid phase multiple component combinatorial array syntheses strategies include U.S. patent application Ser. No. 08/092,862 filed Jan. 13, 1994, which is assigned to the assignee of the present invention, and which is incorporated herein by reference.

Other synthetic strategies that may be employed by the present invention are described in, for example, Bunin et al., "The Combinatorial Synthesis and Chemical and Biological Evaluation of a 1,4-Benzodiazepine Library," Proc. Natl. Acad. Sci. 91:4708–12 (1994) and U.S. Pat. No. 5,288,514, entitled "Solid Phase and Combinatorial Synthesis of Benzodiazepine Compounds on a Solid Support," issued Feb. 22, 1994; and Chen et al., "'Analogous' organic Synthesis of Compound Libraries: Validation of Combinatorial Chemistry in Small-Molecule Synthesis," J. Am. Chem. Soc. 116:2661–2662 (1994).

Thus, as those of skill in the art will appreciate, the methods of the present invention may be used with virtually any synthesis strategy, be it chemical, biological or otherwise, that is now known or will be later developed, to generate libraries of oligomers or polymers.

The representation of each library member within the library depends on apportioning the substrates into the proper reaction vessels at each reaction cycle in the synthesis series. In one embodiment the substrates can be pooled at each step mixed and stochastically re-apportioned into reaction vessels for subsequent reaction cycles. For stochastic mixing and apportioning, increasing the number of substrates upon which a single oligomer sequence will be synthesized increases the likelihood that each oligomer sequence will be represented in the library.

In a preferred embodiment the substrates are apportioned in a non-stochastic manner at each reaction cycle. Non-stochastic distribution has two distinct advantages. First, it ensures that each oligomer sequence is represented in the synthesis library, even if only a single substrate is employed for each oligomer sequence. Second, it increases the likelihood that all oligomer sequences are represented in substantially equal quantities in a synthesized library.

The non-stochastic redistribution process at each reaction cycle will be dictated by the composition of the library. Generally, the composition of any library can be described as a series of sequential matrix calculations. The number of different transformation events at each synthesis cycle is represented by a horizontal "chemical input" matrix. The composition of the library at the beginning of each cycle is defined by a "library matrix". The composition of the library at the completion of any cycle is the product of the library matrix (from the beginning of the cycle) and the chemical input matrix for the cycle just completed.

The matrix notation can be best illustrated by way of specific example. If one desires to construct the complete set of linear oligomer trimers composed of four different monomer inputs A, B, C, and D ($4^3$=64 library members), the chemical input matrix at each cycle is [A, B, C, D]. Thus, at the end of the first monomer addition step, the library matrix is the vertical matrix $$\begin{bmatrix} A \\ B \\ C \\ D \end{bmatrix}_1,$$

where the subscript denotes the reaction cycle number in the series of synthesis reaction cycles.

The composition of the library following the second round of transformation events (here monomer addition reactions) is obtained by taking the product of the chemical input matrix for cycle two and the library matrix from cycle one. Here, the composition of the library at the end of the second reaction cycle is given by:

$$[A,\ B,\ C,\ D]_2 \times \begin{bmatrix} A \\ B \\ C \\ D \end{bmatrix}_1 = \begin{bmatrix} AA & AC & AB & AD \\ BA & BC & BB & BD \\ CA & CC & CB & CD \\ DA & DC & DB & DD \end{bmatrix}_2$$

The composition of the complete set of trimers (i.e. at the end of the third reaction cycle) is given by:

$$[A,\ B,\ C,\ D]_2 \times \begin{bmatrix} AA & AC & AB & AD \\ BA & BC & BB & BD \\ CA & CC & CB & CD \\ DA & DC & DB & DD \end{bmatrix}_2 =$$

$$\begin{bmatrix} AAA & ACA & ABA & ADA & AAB & ACB & ABB & ADB \\ BAA & BCA & BBA & BDA & BAB & BCB & BBB & BDB \\ CAA & CCA & CBA & CDA & CAB & CCB & CBB & CDB \\ DAA & DCA & DBA & DDA & DAB & DCB & DBB & DDB \\ \\ AAC & ACC & ABC & ADC & AAD & ACD & ABD & ADD \\ BAC & BCC & BBC & BDC & BAD & BCD & BBD & BDD \\ CAC & CCC & CBC & CDC & CAD & CCD & CBD & CDD \\ DAC & DCC & DBC & DDC & DAD & DCD & DBD & DDD \end{bmatrix}_3$$

This matrix notation illustrates the redistribution process that must take place at each reaction cycle to generate a library of a particular composition. Specifically, at each reaction cycle each set of substrates in a particular reaction vessel must be divided into subsets, where the number of subsets is equal to the number of different transformation events at that cycle. The exact distribution process will depend on the composition of the library, and will be readily apparent to those skilled in the art upon review of this disclosure.

In one preferred embodiment the substrates can be manually sorted and reapportioned at each retention cycle. This can be illustrated by way of specific example for a library comprising the complete set of $N^{Xn}$ oligomers composed of $X_n$ monomer inputs assembled in N reaction cycles. For the first monomer addition reaction $N^{Xn}$ substrates are divided into $X_n$ reaction vessels, $N^{Xn}/X_n$ substrates per vessel. Integer multiples of $N^{Xn}$ substrates may also be used. After addition of the first monomer inputs $X_1$, $X_2$, . . . $X_n$, the substrates in each of the $X_n$ vessels are divided into $X_n$ aliquots and reapportioned into the $X_n$ vessels, one aliquot per vessel. Following the second reaction cycle each library member can be represented as $NX_{n1}X_{n2}$, where $X_{n1}$ represents the first monomer added to the substrate and $X_{n2}$ represents the second monomer added to the substrate.

For the third monomer addition step, each subset of substrates $NX_{n1}X_{n2}$ is divided into $X_n$ aliquots and reapportioned into the $X_n$ reaction vessels, one aliquot per vessel. Repeating this process N times generates the complete set of oligomers comprised of $X_n$ monomer inputs.

Modifications of this exemplary approach are also possible. For example, one may use any series of transformation events at any reaction cycle. The set of transformation events may be expanded or contracted from cycle to cycle; or the set of transformation events could be changed completely for the next cycle (e.g. couple a monomer in one cycle, rearrange stereochemistry in another cycle). Additionally, one can fix certain transformation events at some cycles while varying other transformation events, to construct oligomer frameworks wherein certain residues or regions within oligomers are altered to provide diversity.

In another preferred embodiment the substrates are sorted and re-apportioned at each cycle using automated sorting equipment. Substrates are placed in a mechanical hopper which introduces them into a vibratory sorter apparatus such as are commonly employed in the manufacturing industry to sort small objects. The vibratory sorter introduces the substrates one at a time into a delivery chute. Attached to the chute is a detector which can scan the identifier tag and receive a unique identifier code. When the code is received the substrate is released from the chute and drops into a reaction vessel. A conveyor system may be used to position one of a series of reaction vessels under the sorter chute for receipt of the substrate. After the identifier tag has been read the conveyor system may then be positioned such that the correct reaction vessel is positioned under the chute to sort individually or in groups as desired.

III. Identifying the Sequence of Any Oligomer

The present invention provides methods for identifying the structure of any of the oligomers in the library. By tracking the synthesis pathway that each oligomer has taken, one can deduce the sequence of any oligomer in a given library. The method involves linking an identifier tag to an oligomer that indicates the series of transformation events, and corresponding synthesis cycles in which those transformation events were experienced, that an oligomer has experienced during construction of a labeled synthetic oligomer library. In one embodiment, after a series of synthesis cycles and concurrent identifier tag detections, one tracks the transformation events to which a particular identifier tag, and thus oligomer, was subjected at each synthesis cycle to determine the oligomer structure. In another embodiment, after a series of synthetic cycles and concurrent identifier tag additions, one "reads" the identifier tag associated with an oligomer to determine the structure of the particular oligomer.

The identifier tags therefore identify each transformation event that an individual oligomer library member has experienced. In addition, a record of the synthesis cycle in the synthesis series at which each transformation event was experienced is generated ("reaction histogram"). As described above, the identifier tags may be pre-encoded with unique identifier information prior to synthesis, or can be encoded with information immediately before, during, or after each transformation event. Methods employing pre-encoded identifier tags, and thus wherein a unique identifier tag is assigned to each library member prior to synthesis, require a number of unique identifier tags equal to the number of library members. Methods employing encodable identifier tags and wherein identifier information is added at each transformation event require only as many unique identification labels, which labels uniquely identify particular transformation events, as there are different transformation events in the synthesis cycle. Unique identifier tags identifying the structure of each oligomer in the library are generated concomitant with synthesis as identification labels identifying each transformation event are added, preferably in a sequential fashion, to the encodable identifier tags at each synthesis cycle. In this latter embodiment the identifier tags preserve a sequential record of which particular transformation events a substrate experienced at each synthesis cycle.

IV. Types of Identifier Tags

The identifier tags of the instant invention may be any detectable feature that permits elucidation of the structure of each oligomer synthesized in a given labeled library. Thus, identifier tags may be, for example: microscopically distinguishable in shape, size, color, optical density, etc.; differentially absorbing or emitting of light; chemically reactive; pre-encoded with optical, magnetic or electronic information; or in some other way distinctively marked with the required decipherable information.

In a preferred embodiment of the invention, the identifier tags relate information back to a detector when pulsed with electromagnetic radiation.

In a more preferred embodiment the identifier tags are microchips that are either pre-encoded or encodable with a unique radiofrequency "fingerprint" that can be detected by pulsing the identifier tag with electromagnetic radiation.

The radiofrequency fingerprint may be a single radiofrequency band, or a combination of radiofrequency bands. When pulsed with electromagnetic radiation, the identifier tags emit a radiofrequency fingerprint that is detected by an electromagnetic radiation detector. Therefore it can be appreciated that the number of unique radiofrequency identifier tags, or "fingerprints," that are available is virtually limitless.

The identifier tags of the present invention can be pre-encoded with unique identifier information prior to synthesis of a labeled synthetic oligomer library. For example, an identifier tag may be a bar code strip that corresponds to, say, the number 001, or it may be a radiofrequency fingerprint comprised of one or a plurality of frequency bands. Each library member is thus labeled with a unique, static identifier tag throughout the combinatorial synthesis, or in a "birth-to-death" fashion.

The identifier tags may also be encodable with new information from time to time. For example, the identifier tag may be a bar code strip that can receive sequential information from time to time or a microchip that can be "downloaded" with digital information from time to time. The encodable identifier tags may be either blank or pre-encoded with partial or complete identifier information prior to synthesis of a labeled synthetic oligomer library.

Each transformation event in a series of reaction cycles in the synthesis of a labeled synthetic oligomer library is assigned a unique identification label, which label is added to the encodable identifier tag either concomitant with, or close in time to, performance of a particular transformation event. At the termination of a synthesis comprising an unlimited number of reaction cycles and transformation events, a unique sequential signal has been downloaded onto the microchip such that the history of transformation events to which the encodable substrate was subjected is recorded in a sequential fashion on the microchip. The oligomer sequence can therefore be deduced by detecting the unique sequential identification information contained in the identifier tag.

In another preferred embodiment the identifier tags of the present invention are encased in a glass or polymeric material. Such glass or polymeric material may be readily attached to synthesis supports, directly derivatized with one or a plurality of functional groups suitable for synthesis, or directly derivatized with one or a plurality of linkers bearing one or a plurality of functional groups suitable for synthesis. It can be readily appreciated that the identity of such functional groups will be dictated by the composition of the desired oligomers. Suitable groups will be readily apparent to those skilled in the art and include, but are not restricted to, amino, carboxyl, sulfhydryl, hydroxyl, and the like.

Any glass or polymeric material capable of encasing an identifier tag can be used in the present invention. In one mode such polymeric material is capable of being derivatized with one or a plurality of functional groups or linkers suitable for synthesis. Polymers such as polyethylene glycol polystyrene-divinyl benzene, polyethylene grafted polystyrene, polyacrylamide-kieselguhr composites and glass have all been commercialized with functional groups suitable for derivatized with various linkers and monomers. Methods for derivatizing such polymers are well known in the art. See, e.g., Atherton and Sheppard, Solid Phase Peptide Synthesis: A Practical Approach, IRL Press at Oxford University Press, Oxford, England (1989), and Gait, Oligonucleotide Synthesis: A Practical Approach, IRL Press at Oxford University Press, Oxford, England (1984), each of which is incorporated herein by reference.

Suitable preferred identifier tags are well known in the art and are described, for example, in U.S. Pat. No. 5,252,962, entitled "System Monitoring Programmable Implantable Transponder," issued on Oct. 12, 1993, to Bio Media Data Systems, Inc. and U.S. Pat. No. 5,351,052, entitled "Transponder System for Automatic Identification Purposes," issued on Sept. 27, 1994, to Texas Instruments, Inc., each of which is incorporated herein by reference. Commercially available examples include ELAMS™ (Electronic Laboratory Animal Monitoring Systems), manufactured by Biomedic Data Systems, 225 West Spring Valley Ave., Maywood, N.J. 07607, and TIRIS™ (Texas Instruments Registration and Identification System), manufactured by Texas Instruments, 12501 Research Blvd., Mailstop 2243, Austin, Tex. 78759.

ELAMS™, which are widely used to tag and identify laboratory mice via subcutaneous injection of the ELAMS™, comprise glass-encased microchips that are pre-tuned to emit a unique radiofrequency fingerprint when pulsed with electromagnetic radiation. TIRIS™, which are currently used for security cards and to track and identify livestock and automobiles, comprise glass-encased microchips that can be downloaded with digital information from time to time.

ELAMS™ and TIRIS™ possess a variety of features that make them ideally suited for use as combinatorial chemistry library identifier tags. For example, ELAMS™ and TIRIS™ can be readily sorted using currently available automated sorter technology. In addition, the encoded information can be scanned and stored in a microcomputer. Furthermore, ELAMS™ and TIRIS™ are compatible with virtually any chemistry now known or that will be later developed to generate oligomer or polymer libraries. Thus, large labeled libraries of virtually any chemical composition can be generated in an automated fashion, thereby increasing the diversity of labeled libraries available while decreasing the time and effort necessary to generate such libraries.

V. Linking the Oligomers to the Identifier Tags

An oligomer of the present invention may be linked to an identifier tag in a variety of fashions. See, for example, FIG. 7. One or a plurality of oligomers of identical sequence can be attached directly to one or a plurality of functional groups on an identifier tag, to one or a plurality of linkers that are attached to an identifier tag, or to one or a plurality of synthesis supports that are attached to an identifier tag. An identifier tag may also be retained within a frame or housing to which one or a plurality of oligomers of identical structure are attached. Additionally, an identifier tag may be retained within a frame or housing that also retains one or a plurality of synthesis supports having attached thereto one or a plurality of oligomers of identical structure.

In one preferred embodiment one or a plurality of oligomers of identical structure are attached directly to one or a plurality of functional groups on an identifier tag. Typically, the identifier tag will be encased in a glass or polymeric material that can be derivatized with one or a plurality of functional groups suitable for synthesis. Any polymeric material capable of providing functional groups suitable for attachment can be utilized. It can be readily appreciated that the identity of the functional groups will be dictated by the composition of the desired oligomers. Suitable groups will be readily apparent to those skilled in the art and include, but are not limited to, amino sulfhydryl, hydroxyl, and the like.

Several polymeric materials have been commercialized with suitable functional groups such as, for example, polystyrene-divinyl benzene, polyethylene grafted polystyrene, polyacrylamide kieselguhr composite and controlled pore glass. Methods for derivatizing such polymers are well known in the art. See, e.g., Atherton and Sheppard, Solid Phase Peptide Synthesis: A Practical Approach, IRL Press at Oxford University Press, Oxford; England (1989), and Gait, Oligonucleotide Synthesis: A Practical Approach, IRL Press at Oxford University Press, Oxford, England (1984), each of which is incorporated herein by reference.

Alternatively, one or a plurality of oligomers of identical structure may be attached to the functional groups on an identifier tag by means of a linker. A linker is generally a moiety, molecule, or group of molecules attached to a synthesis support or substrate and spacing a synthesized polymer or oligomer from a synthesis support or substrate.

Typically a linker will be bi-functional, wherein said linker has a functional group at one end capable of attaching to a monomer, oligomer, synthesis support or substrate, a series of spacer residues, and a functional group at another end capable of attaching to a monomer, oligomer, synthesis support or substrate.

The functional groups of a bifunctional linker need not be identical, thereby allowing the linker to act as a "functional group adapter." Thus, bifunctional linkers provide a means whereby the functional group displayed on a substrate or synthesis support, say an amino group, can be converted into a different functional group, say a hydroxyl group. The use of bifunctional linkers can therefore greatly increase the repertoire of chemistries that can take advantage of solid phase synthesis strategies.

The composition and length of the linker will depend in large part upon the application of the library. The degree of binding between an immobilized library member and its binding partner may in some embodiments depend on the accessibility of the immobilized library member to its binding partner. The accessibility in turn may depend on the length and/or chemical composition of the linker moiety.

The composition of the linker moiety will also depend on the desired properties of the linker, and in large part will be dictated by the physical conditions and/or biological or chemical reagents to which the linker will be exposed during synthesis. For example, one may desire a rigid linker, such as for example, poly-proline or poly-allyl, or one may desire a flexible linker such as, for example polyalanine or saturated hydrocarbons.

It is desirable that the linker be stable to the reaction conditions used to construct the library. Linkers of suitable composition will be readily apparent to those skilled in the art, or may be later developed.

The number of spacer residues that comprise the linker may also vary. Typically, a linker will generally comprise about 1–100 spacer residues, preferably about 1–20 spacer residues, and usually about 5–15 spacer residues.

Spacer residues may be atoms capable of forming at least two covalent bonds, such as carbon, silicon, oxygen, nitrogen, sulfur, phosphorous, and the like. Spacer residues may also be molecules capable of forming at least two covalent bonds such as amino acids, nucleosides, nucleotides, sugars, aromatic rings, hydrocarbon rings, carbohydrates, branched or linear hydrocarbons, and the like. Thus, the interlinkages comprising the linker include, but are not limited to, amides, ethers, esters, ureas, phosphoesters, thioesters, thioethers, and the like. The interlinkages connecting spacer residues may be, but need not be, identical.

Linked together, the spacer residues may form linear, cyclic, branched, or other types of structures. Thus, a linker may provide a plurality of functional groups to which oligomers may be attached, thereby increasing the quantity of oligomer synthesized. Linked together the spacer residues may be rigid, semi-rigid or flexible. The spacer residues comprising the linker may be, but need not be, identical.

Such linker moieties may be capable of later releasing the synthesized molecules by some specific, regulatable mechanism. Such regulatable mechanisms include but are not restricted to thermal, photochemical, electrochemical, acid, base, oxidative and reductive reactions. Several linkers which provide a variety of functional group coupling and cleavage strategies are commercially available.

As will be readily apparent to the skilled artisan upon review of this disclosure, the labeled combinatorial synthesis methods and apparatus described herein can be used to optimize linker composition and length.

In another preferred embodiment, one or a plurality of oligomer of identical structure may be attached to one or a plurality of synthesis supports that are attached to an identifier tag. An oligomer may be covalently attached directly to a functional group on the synthesis support, or may be attached to a synthesis support by means of a linker as described above. In one preferred embodiment one or a plurality of synthesis supports are attached to an identifier tag by physical means such as glue or magnetic attraction. Virtually any physical means that is stable to the reaction conditions employed to synthesize the library may be used.

In another preferred embodiment, one or a plurality of synthesis supports is covalently attached to an identifier tag (optionally encased in a glass or polymeric coating). Such covalent attachment can be either directly to one or a plurality of functional groups on the identifier tag, or by means of a linker as described above.

In yet another preferred embodiment an identifier tag may be retained within a frame or housing, which frame or housing also retains one or a plurality of oligomers of identical structure or one or a plurality of synthesis supports having attached thereto one or a plurality of oligomers of identical structure. Such oligomer attachment may be either directly to a functional group on the synthesis support, or may be mediated by a linker as described above.

In still another preferred embodiment an identifier tag may be retained in a frame or housing, which frame or housing has attached thereto one or a plurality of oligomers of identical structure. Such oligomer attachment may be either directly to a functional group on the frame or housing, or may be mediated by a linker as described above.

VI. Encoding the Identifier Tag Information

A variety of types of information may be encoded on the identifier tags of the present invention. For example, the identifier tags may be pre-encoded with a bar code strip, moieties which differentially absorb or emit light, magnetic or optical information, or any other uniquely identifiable and detectable mark. Thus, the means employed for encoding the identifier tag information is dictated by the means employed for detecting the encoded identification signal.

In a preferred embodiment, an identifier tag comprises a microchip that is imprinted with a unique radiofrequency "fingerprint" that is transmitted back to a detector when the identifier tag is pulsed with electromagnetic radiation. In this embodiment, a microchip is exposed to a beam comprising one or a plurality of radiofrequency bands. The microchip draws power from the beam. The microchip has an electronic fingerprint. Thus, microchips of different fingerprints will emit different signals when pulsed with electromagnetic radiation. Accordingly, each of a plurality of microchips can be pre-encoded with a unique "fingerprint" or identification label. The skilled artisan will appreciate that the number of microchips that can be imprinted with a unique identification label is virtually without limit. Such microchips are well known in the art, and are described in, for example, U.S. Pat. No. 5,148,404, entitled "Transponder and Method for the Production Thereof," issued on Sept. 15, 1992, to Texas Instruments, Inc., and which is incorporated herein by reference.

In another preferred embodiment an identifier tag comprises a microchip that can be imprinted with digital or sequential information at each reaction cycle in a series of reaction cycles. The identifier tag can be either pre-encoded with partial or complete identifier information or blank prior to synthesis of a labeled synthetic oligomer library. Concomitant with, or at a point close in time to, each reaction cycle a new multi-digit identifying the transformation event a particular encodable substrate experienced is downloaded to the identifier tag such that a history of transformation events to which the identifier tag was subjected is recorded. Since the identifier information at each cycle is added sequentially to the microchip, each oligomer structure can be elucidated by detecting the sequential digital information contained in the identifier tag linked to that particular oligomer. Suitable digitally encodable substrates and encoding methods are well known or will be apparent to those skilled in the art, and are described in, for example U.S. Pat. No. 5,351,052, entitled "Transponder Systems for Automatic Identification Purposes," issued on Sept. 27, 1994 to Texas Instruments, Inc. and U.S. Pat. No. 5,252,962, entitled "System Monitoring Programmable Implantable Transponder," issued on Oct. 12, 1993, to Bio Medic Data Systems, Inc., each of which is incorporated herein by reference.

VII. Recovering and Decoding the Identifier Tag Information

When specific library members are isolated in a receptor screening experiment, the substrates can be segregated individually by a number of means, including: micromanipulation, magnetic attraction, sorting, or fluorescence activated cell sorting (FACS), although with respect to the present invention FACS is more accurately "fluorescence activated oligomer sorting." See Methods in Cell Biology, Vol. 33, Darzynkiewicz, Z. and Crissman, H. A. eds., Academic Press; and Dangl and Herzenberg, J. Immunol. Methods 52:1–14 (1982), both of which are incorporated herein by reference.

Once the desired substrates have been isolated, the identity of the identifier tag must be ascertained to obtain the structure of the oligomer on the substrate. The method of identification will depend on the type of identifier tag used to encode the library. For example, bar code identifier tags can be scanned with laser devices commonly employed in the art to read bar codes. Fluorescent identifier tags can be read by obtaining a fluorescence spectrum.

In preferred embodiments employing microchip identifier tags, the identifier tag information can be read using detection devices commonly employed in the art to scan and store identifier information from such tags. Typically such detectors can scan, display, transmit and store identifier information received from an identifier tag. Such detectors are well known in the art and are described, for example, in U.S. Pat. No. 5,262,772, entitled "Transponder Scanner" issued Nov. 16, 1993, to Bio Medic Data Systems, Inc., which is incorporated herein by reference. Such systems that read, display, transmit and store identifier information and that can be interfaced with a microcomputer are commercially available, including Bio Medic Data Systems models DAS-4004EM, DAS-40020A and DAS-4001.

In preferred embodiments, the detection system employed will be interfaced with a computer to automate identifier tag information storage. In even more preferred embodiments the detection equipment will be interfaced with a computer and automated sorting equipment.

VIII. Screening Receptors with Labeled Synthetic Oligomer Libraries

The labeled synthetic oligomer libraries of the present invention will have a wide variety of uses. By way of example and not limitation, labeled synthetic oligomer libraries can be used to identify peptide, nucleic acid, carbohydrate and/or other structures that bind to proteins, enzymes, antibodies, receptors and the like; identify sequence-specific binding drugs; identify epitopes recognized by antibodies; evaluate a variety of drugs for clinical diagnostic applications; identify materials that exhibit specific properties, such as, for example, ceramics; identify elements comprising superconducting compositions; combinations of the above; and other uses that will be apparent to those skilled in the art.

Synthetic oligomers displayed on substrates can be screened for the ability to bind to a receptor. The receptor may be contacted with the library of synthetic oligomers, forming a bound member between a receptor and the oligomer capable of binding the receptor. The bound member may then be identified. As one example, the receptor may be an antibody.

The techniques for selection of individual substrates displaying ligands on their surface are analogous to FACS methods for cloning mammalian cells expressing cell surface antigens and receptors. Therefore, methods for selecting and sorting substrates will be readily apparent to those skilled in the art of cell sorting. For example, a receptor can be labelled with a fluorescent tag and then incubated with the mixture of substrates displaying the oligomers. After washing away un-bound and non-specifically bound receptors, one can then use FACS to sort the beads and to identify and isolate physically individual beads showing high fluorescence. Alternatively, if the physical size of the substrates permits, one can manually identify and sort the substrates showing high fluorescence.

Alternatively, the present invention can be used to generate libraries of soluble labeled oligomers, which can be used with a variety of screening methods. For instance, The substrates can be sorted and placed in individual compartments or wells, such as, for example, the wells of a 96-well microtitre plate. The oligomers are cleaved from the substrates and remained contained within the well along with the identifier tag. The library members may then be assayed in solution by a variety of techniques that will be readily apparent to those skilled in the art of immunology, one example of which is described below.

In one embodiment the bottom surface of each well is coated with the receptor. After addition of the binding buffer and a known ligand for that receptor that is fluorescently labelled, one effectively has a solution phase competitive assay for novel ligands of the receptor. The binding of the fluorescently labelled ligand to the receptor is estimated by confocal imaging of the monolayer of immobilized receptor. Wells showing decreased fluorescence on the receptor surface indicate that the released oligomer competes with the labelled ligand. The substrates in the wells showing competition are recovered, and the identifier tag decoded to reveal the sequence of the oligomer.

EXAMPLE I

Synthesis of One-hundred Amides

One hundred unique identifier tags containing Rink polymer are subdivided into ten groups of ten, and each group of ten is introduced into a separate 250 mL reaction vessel charged with 100 mL of methanol solvent. To each reaction vessel is then added 10 mL of a solution containing an aldehyde dissolved in methanol, a different aldehyde added to each reaction vessel.

The reaction is stirred for six hrs at room temperature, or until completion of the reaction. The reaction may be monitored using standard techniques for the monitoring of solid phase reactions. After completion of the reaction, the solvent and excess reagents are removed from each of the ten reaction vessels independently, and the polymer in each vessel washed three times with methanol and dichloromethane and allowed to dry using reduced pressure.

The unique identifier tags are then recorded by removing the contents of each reaction vessel and passing the unique identifier tag by a detector. The unique identifier tag for each oligomer is thus recorded and cross-referenced to the reaction vessel from which it was removed.

The unique identifier tags associated with the Rink polymer are then randomly recombined and again subdivided into ten groups of ten, and each group of ten placed into a different reaction vessels (250 mL) containing 100 mL dichloromethane. Each of the ten reaction vessels is charged with base, and ten unique acid chlorides are introduced into the reaction vessels, one acid chloride per vessel.

The reactions are allowed to proceed to completion. The reactions may be monitored using standard methods. After completion, the solvent is removed by filtration and the oligomer in each reaction vessel is washed independently with three washes each of methanol and dichloromethane. Each of the ten identifier tags is then removed from each vessel and passed by a detector to record their unique identification numbers.

Thus, each identification number is associated with a specific reagent utilized in the first step of the synthesis (an aldehyde) and the second step of the synthesis (an acid chloride), providing a unique "reaction histogram" for each of the one hundred unique identifier tags.

After completion of the reaction, the identifier tags associated with each polymer are separately deblocked using trifluoroacetic acid and introduced into a microtiter plate such that each well of the microtiter plate contains only a single polymer. After removal of solvent and evaporation to dryness, each well contains a unique structure.

The decoding of said structure can be accomplished by comparing the individual identifier tag with histogram for that particular tag. That is, the identifier tag will be associated with a specific structure for the aldehyde monomer input and a specific structure for the acid chloride monomer input. The structure of the polymer contained in each well is thus known unequivocally.

EXAMPLE II

Synthesis on ELAMS™ of Four Pentapeptides

A. Derivatization of ELAMS™

Four (or multiples thereof) ELAMS™ (Biomedic Data Systems), each having a unique identifier tag are washed with refluxing aqueous $HNO_3$ for 20 min. The ELAMS™ are pelleted and washed with distilled water (5×) and methanol (3×) and dried at 125° C. for about 12 hours. The ELAMS™ are then vortexed in with a solution of 5% (v/v) aminopropyltriethoxysilane in acetone for ten hours, washed with acetone (2×), ethanol (5×) and methylene chloride (2×) and dried at 125° C. for 45 min.

The ELAMS™ are suspended in anhydrous DMF (1 mL) containing diisopropylethylamine (DIEA) (17 μL, 100 μmoles) and a solution of Fmoc-b-alanine pentafluorophenyl ester (200 mg, 420 μmoles, Peninsula Labs) in distilled water (1.5 mL) added. After treatment with shaking for about 12 hours the ELAMS™ can be collected and washed with DMF (3×) and methylene chloride (2×). ELAMS™ are treated with a solution of 10% acetic anhydride in DMF containing 0.05 mol of 4-dimethylaminopyridine to cap uncoupled aminopropyl groups and then washed with DMF (2×) and methylene chloride (2×). ELAMS™ are then vortexed with a solution of 20% piperidine in DMF to release the Fmoc protecting group. The Fmoc-piperidine adduct can be quantitated by monitoring the absorbance spectrum of the supernatant at 302 nm ($\epsilon_{302}$=7800 $M^{-1}$ $cm^{-1}$) to estimate the degree of substitution of amino groups per quantity of E. Finally, the ELAMS™ are washed with ethanol (5×) and methylene chloride (2×) and dried at 85° C. for about 12 hours.

B. Preparation of Boc-Gly-L-Phe-L-Leu-OH

Glycyl-L-phenylalanyl-L-leucine (552 mg, 1.5 mmol, Bachem) is dissolved in a solution containing distilled water (10 mL) and 1 M NaOH (1.5 mL). The solution is cooled in an ice bath and treated with a solution of di-tert-butyl pyrocarbonate (337 mg, 1.5 mmol) in p-dioxane (12 mL). The solution is stirred for 4 hours at room temperature, after which the solution is concentrated to dryness in vacuo, the residue taken up in water (5 mL) and the pH adjusted to 2.5 by the addition of 1 M $KHSO_4$. The aqueous suspension is extracted with ethyl acetate (2×, 15 mL), the organic layer separated and dried over magnesium sulfate. After removal of the solvent in vacuo the residue can be titurated with hexane to yield Boc-Gly-L-Phe-L-Leu-OH as a white solid.

C. Preparation of Gly-L-Phe-L-Leu ELAMS™

Boc-Gly-L-Phe-L-Leu-OH (44 mg, 0.1 mmol), benzotriazol-1-yloxytris(dimethylamino)phosphonium hexaflurophsophate (14 mg, 0.104 mmol) are dissolved in dry DMF (1 mL). DIEA (20 μL, 0.115 mmol) is added and about 0.5–1.0 mL of this solution is transferred to a test tube containing amino derivatized ELAMS™. The tube is sealed, vortexed for about 3.5–4 hours and the ELAMS™ pelleted and washed with DMF (3×) and methylene chloride (2×). The ELAMS™ are then deprotected with a solution of 50% triluoroacetic acid (TFA) is methylene chloride for 30 min., washed with methylene chloride (2×), ethanol (2×) and methylene chloride (2×), and dried at 55° C. for about 1 hour. The identifier tag from each ELAMS™, is detected and recorded.

Preparation of Gly-Gly-L-Phe-L-Leu (SEQ ID NO:5) ELAMS™

Fmoc-glycine pentafluorophenyl ester (46 mg, 0.1 mmol) is dissolved in anhydrous DMF (1 mL) containing DIEA (17 μL, 0.1 mmol). About 0.5–1.0 mL of this solution is added to Gly-L-Phe-L-Leu ELAMS™ in a test tube and the tube vortexed for about 3 hours. The ELAMS™ are pelleted and washed with DMF (4×) and methylene chloride (2×). Deprotection can be effected by treatment with a solution of 20% piperidine in DMF for 30 min. The ELAMS™ are then washed with DMF (2×); ethanol (2×) and methylene chloride (2×) and dried at 60° C. for 4 hours. The identifier tag for each ELAMS™ is detected and recorded.

E. Preparation of L-Pro-Gly-L-Phe-L-Leu (SEQ ID NO:6) ELAMS™

Fmoc-L-proline pentafluorophenyl ester (50 mg, 0.1 mmol) is dissolved in anhydrous DMF (1 mL) containing DIEA (17 μL, 0.1 mmol). About 0.5–1.0 mL of this solution is added to Gly-L-Phe-L-Leu ELAMS™ in a test tube and the tube vortexed for about 3 hours. The ELAMS™ are pelleted and washed with DMF (4×) and methylene chloride (2×). Deprotection can be effected by treatment with a solution of 20% piperidine in DMF for 30 min. The ELAMS™ are then washed with DMF (2×), ethanol (2×) and methylene chloride (2×) and dried at 60° C. for 4 hours. The identifier tag for each ELAMS™ is detected and recorded.

F. Preparation of Tyr-Gly-Gly-L-Phe-L-Leu (SEQ ID NO:1) and Tyr-Pro-Gly-L-Phe-L-Leu (SEQ ID NO:2) ELAMS™

Fmoc-O-t-butyl-L-tyrosine pentafluorophenyl ester (63 mg, 0.1 mmol) is dissolved in anhydrous DMF (1 mL) containing DIEA (17 μL, 0.1 mmol). About 0.5–1.0 mL of this solution is added to Gly-Gly-L-Phe-L-Leu (SEQ ID NO:5) and Pro-Gly-L-Phe-L-Leu (SEQ ID NO:6) ELAMS™ in a test tube and the tube vortexed for about 3 hours. The ELAMS™ are pelleted and washed with DMF (4×) and methylene chloride (2×). Deprotection can be effected by treatment with a solution of 20% piperidine in DMF for 30 min, followed by treatment with a solution of 50% TFA in methylene chloride for 30 min. The ELAMS™ are then washed with DMF (2×), ethanol (2×) and methylene chloride (2×) and dried at 60° C. for 4 hours. The identifier tag for each ELAMS™ is detected and recorded.

G. Preparation of Pro-L-Pro-Gly-L-Phe-L-Leu (SEQ ID NO:3) and Pro-Gly-Gly-L-Phe-L-Leu (SEQ ID NO:4) ELAMS™

Fmoc-L-proline pentafluorophenyl ester (50 mg, 0.1 mmol) is dissolved in anhydrous DMF (1 mL) containing DIEA (17 μL, 0.1 mmol). About 0.5–1.0 mL of this solution is added to Gly-Gly-L-Phe-L-Leu (SEQ ID NO:5) and Pro-Gly-L-Phe-L-Leu (SEQ ID NO:6) ELAMS™ in a test tube and the tube vortexed for about 3 hours. The ELAMS™ are pelleted and washed with DMF (4×) and methylene chloride (2×). Deprotection can be effected by treatment with a solution of 20% piperidine in DMF for 30 min. The ELAMS™ are then washed with DMF (2×), ethanol (2×) and methylene chloride (2×) and dried at 60° C. for 4 hours. The identifier tag for each ELAMS™ is detected and recorded.

H. Selection of ELAMS™ Containing Peptide Ligands for Monoclonal Antibody 3E7

Monoclonal antibody 3E7 can be raised against opioid peptide beta-endorphin. The binding specificity of MAb 3E7 has been well characterized by solution assays with chemically synthesized peptides. The equilibrium binding constants (Kd) of the peptides considered here are as follows: YGGFL (SEQ ID NO:1) is 6.6 nM; and YPGFL (SEQ ID NO:2), PPGFL (SEQ ID NO:3), and PGGFL (SEQ ID NO:4) are each >1 mM; thus, only peptide YGGFL (SEQ ID NO:1) shows appreciable affinity for the antibody.

A mixture of ELAMS™ containing either YGGFL (SEQ ID NO:1), YPGFL (SEQ ID NO:2), PGGFL (SEQ ID NO:4), or PPGFL (SEQ ID NO:3) are added to phosphate buffered saline (PBS) containing monoclonal antibody 3E7 that has been previously conjugated to colloidal superparamagnetic microbeads (Miltenvi Biotec, West Germany). After a 16 hour incubation at 4° C., beads which bind the 3E7 antibody can be selected using a high strength magnet. The identifier information of the selected beads is then analyzed with a model DAS-4001EM or DAS-4001 detector (Bio Medic Data Systems). Analysis will reveal that only ELAMS™ upon which YGGFL (SEQ ID NO:1) was synthesized are selected by the 3E7 antibody.

Alternatively, the ELAMS™ can be incubated with 3E7 antibody that has been previously conjugated with a fluorophore such as fluorescein or rhodamine, and peptide-antibody binding detected with a fluorimeter or epifluorescence microscope using the appropriate wavelength of light

EXAMPLE III

Parrallel Synthesis of Peptides on ELAMS™

A. Derivatizing Amino ELAMS™ with a Linker

ELAMS™ containing amino groups and each having a unique identifier tag are prepared as described in Example II.A., above. The ELAMS™ are treated with a mixture of 4-Fmoc-aminobutyric acid N-hydroxysuccinimide ester (1 mmol), HBTU (1 mmol), HOBt (1 mmol) and DIEA (1 mmol) in 9:1 methylene chloride:DMF (10 mL). After vortex treatment for 30 minutes, the reaction mixture is diluted with DMF (10 mL), the ELAMS™ pelleted, and the supernatant decanted. The ELAMS™ are washed with DMF (3×10 mL). The coupling procedure may be repeated with fresh reagents and the ELAMS™ pelleted and washed as described above.

B. Parallel Synthesis of Peptides

Figure 1:
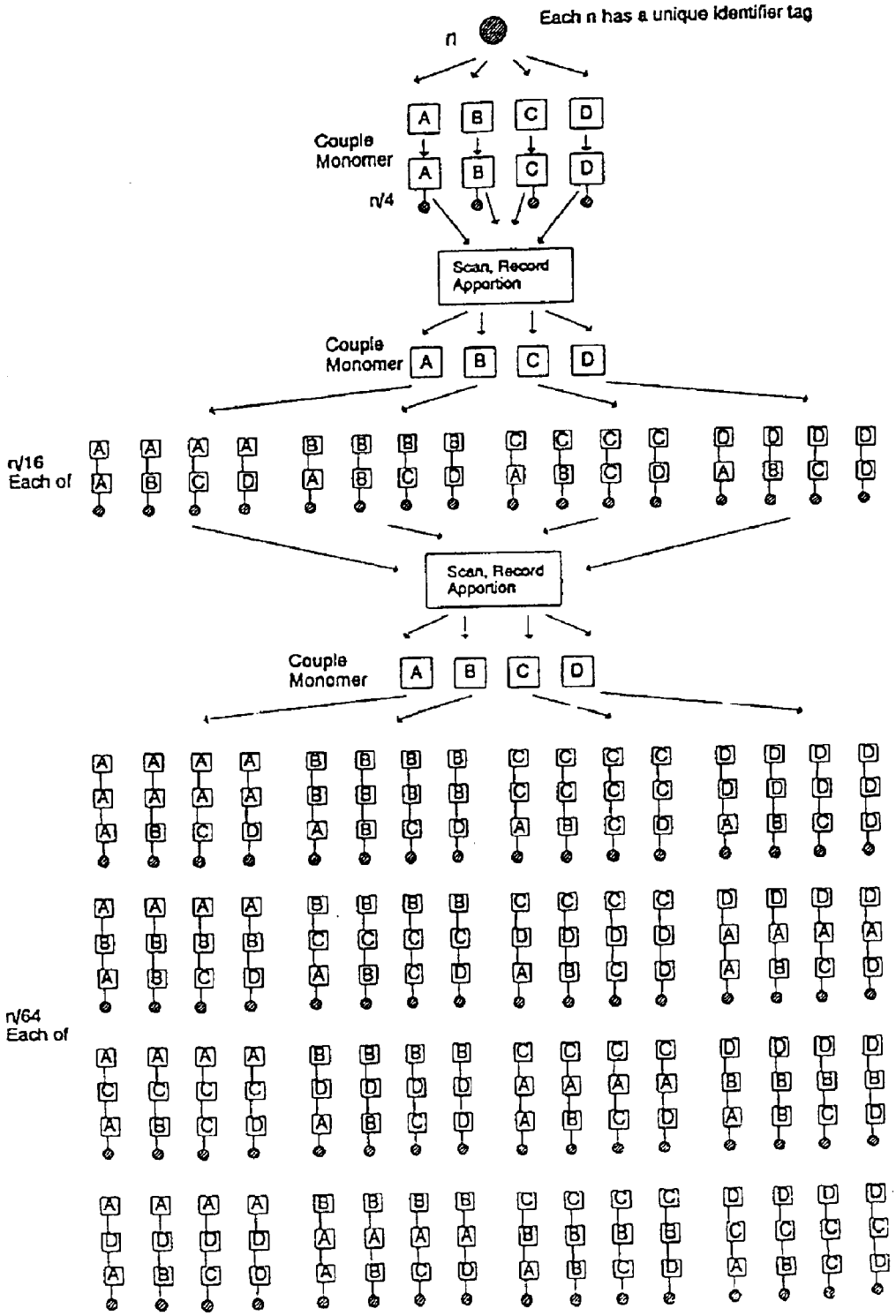
FIG. 1 schematically illustrates the synthesis of the complete set of linear trimers composed of four different monomer inputs using pre-encoded identifier tags.
Figure 2:
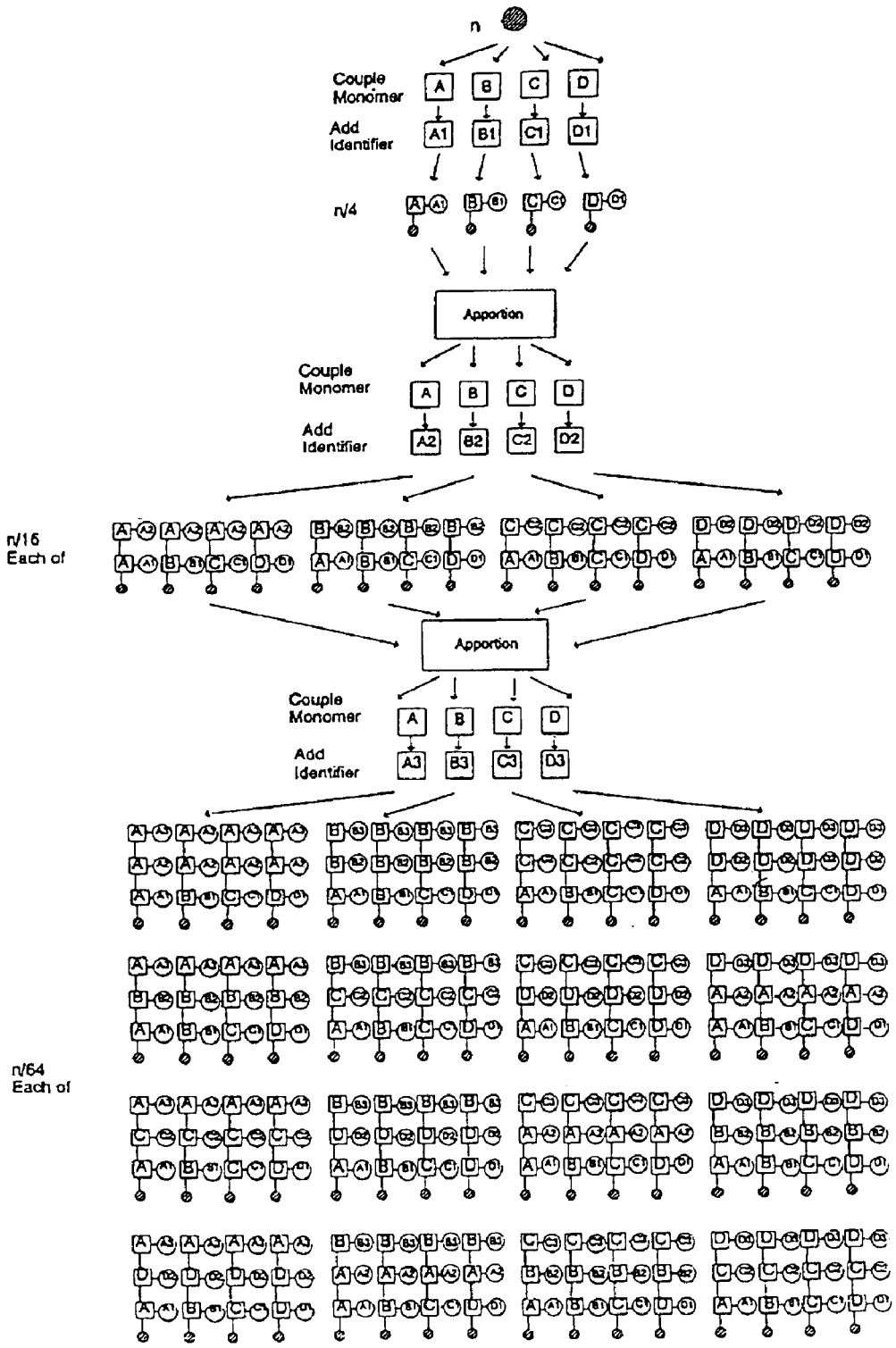
FIG. 2 schematically illustrates the assembly of the complete set of linear trimers composed of four different monomer inputs wherein the identifier tags are encoded with identifier information in parallel with oligomer synthesis.
Figure 3:
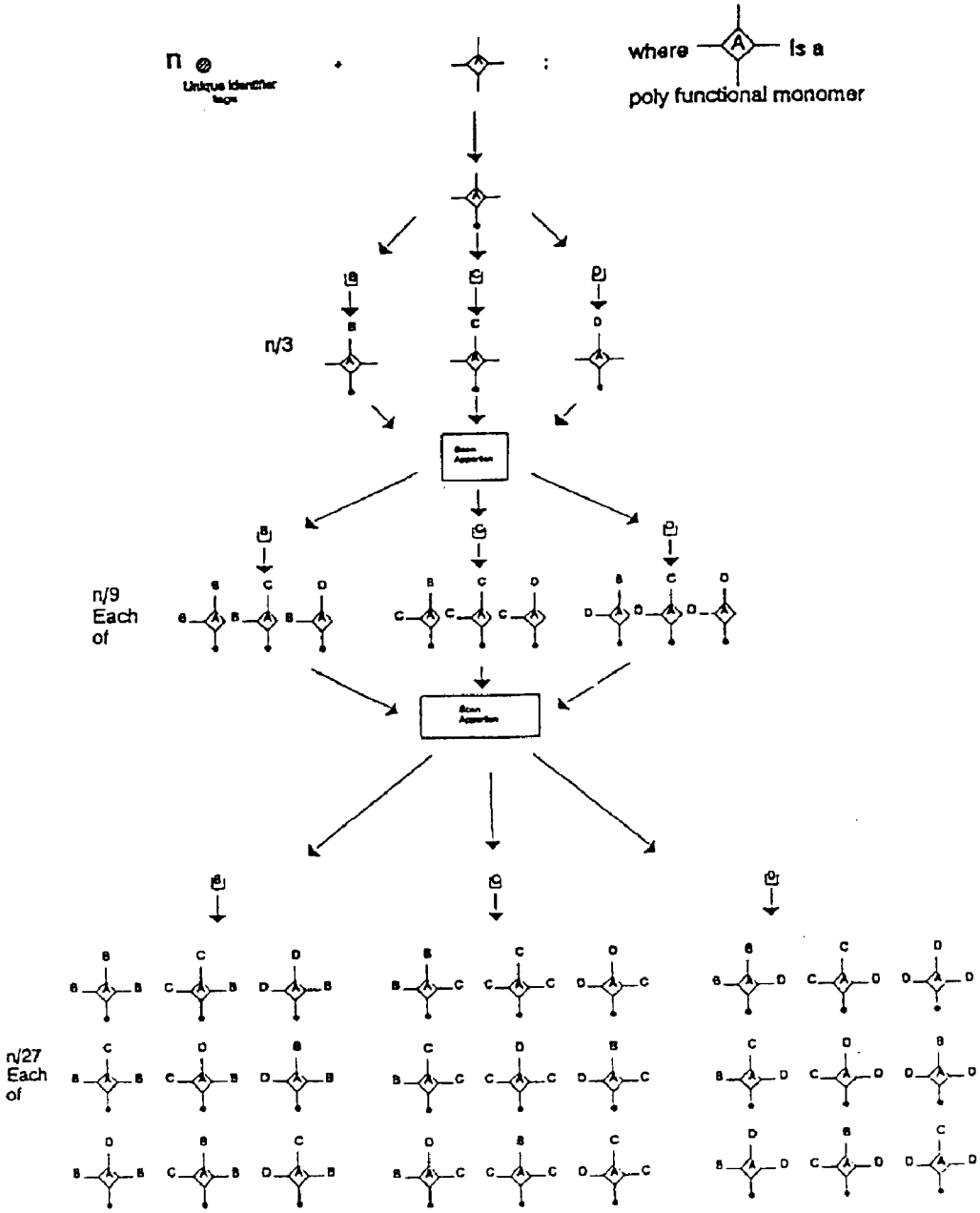
FIG. 3 schematically illustrates the synthesis of a labeled library of oligomers composed of four different monomer inputs and having a common core structure using pre-encoded identifier tags.
Figure 4:
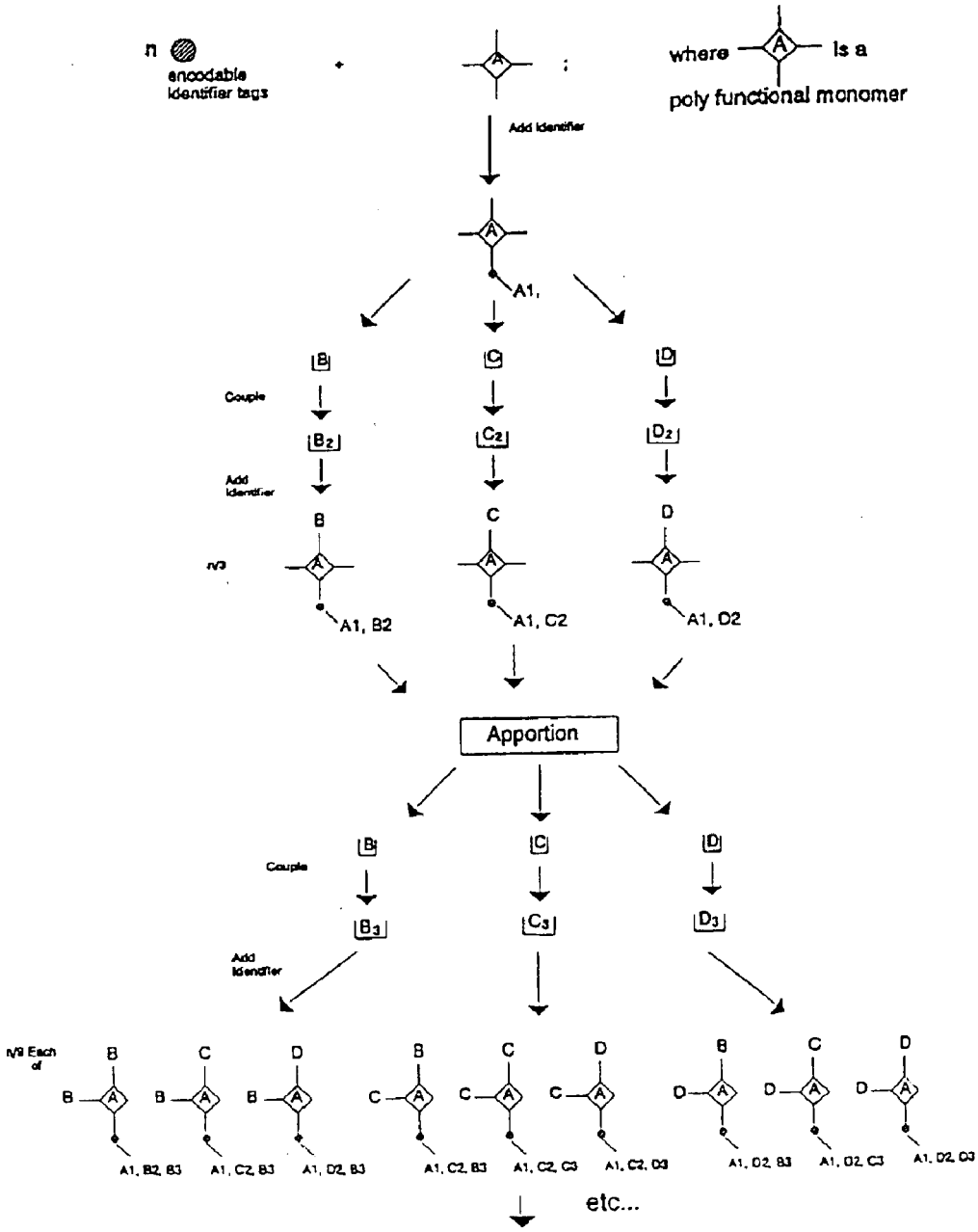
FIG. 4 schematically illustrates the synthesis of a labeled library of oligomers composed of four different monomer inputs and having a common core structure wherein the identifier tags are encoded with identifier information in parallel with oligomer synthesis.
Figure 5:
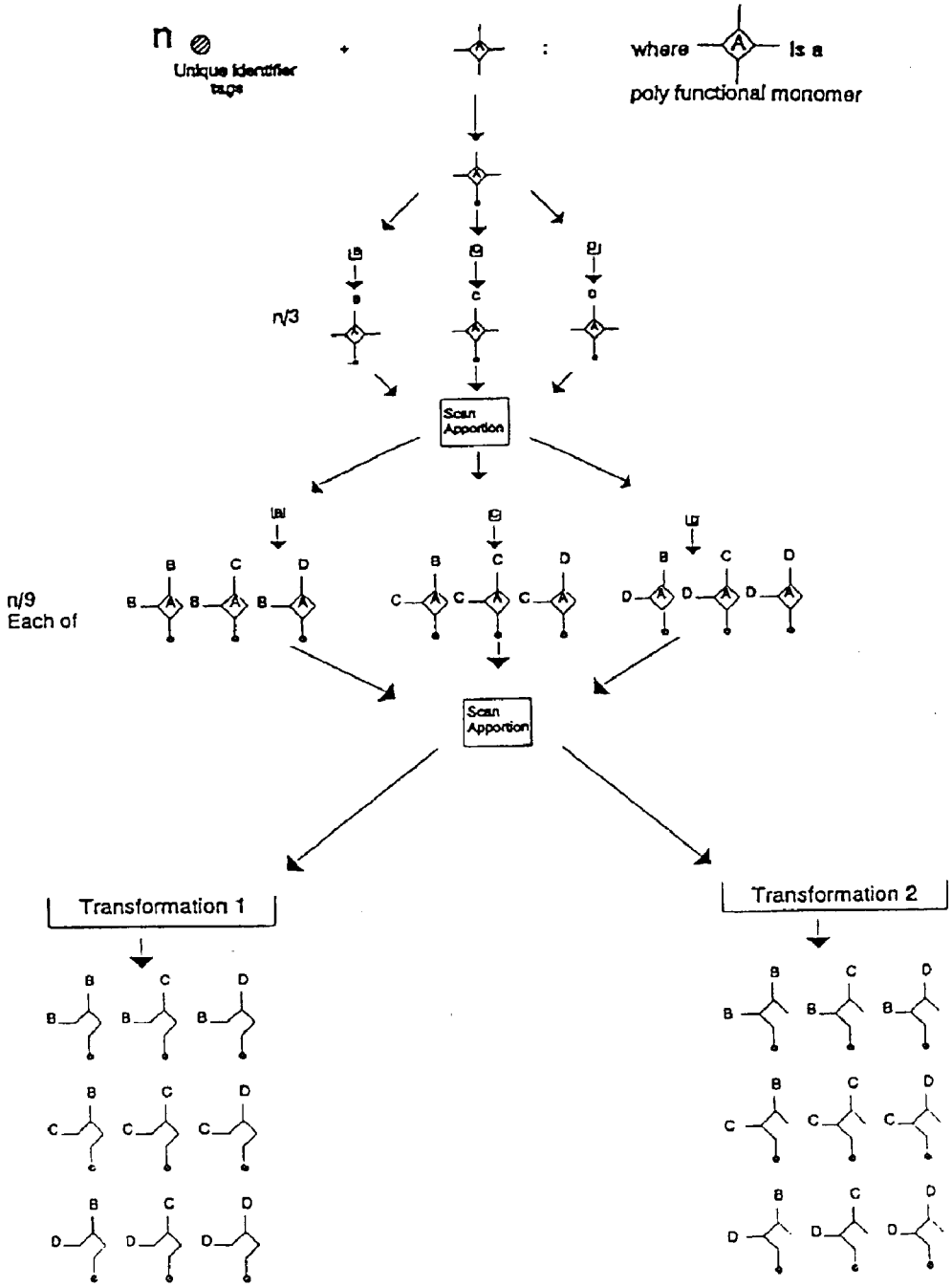
FIG. 5 schematically illustrates the synthesis of a labeled library of oligomers constructed using a multiple cycle synthesis series with a plurality of different transformation events using pre-encoded identifier tags.
Figure 6:
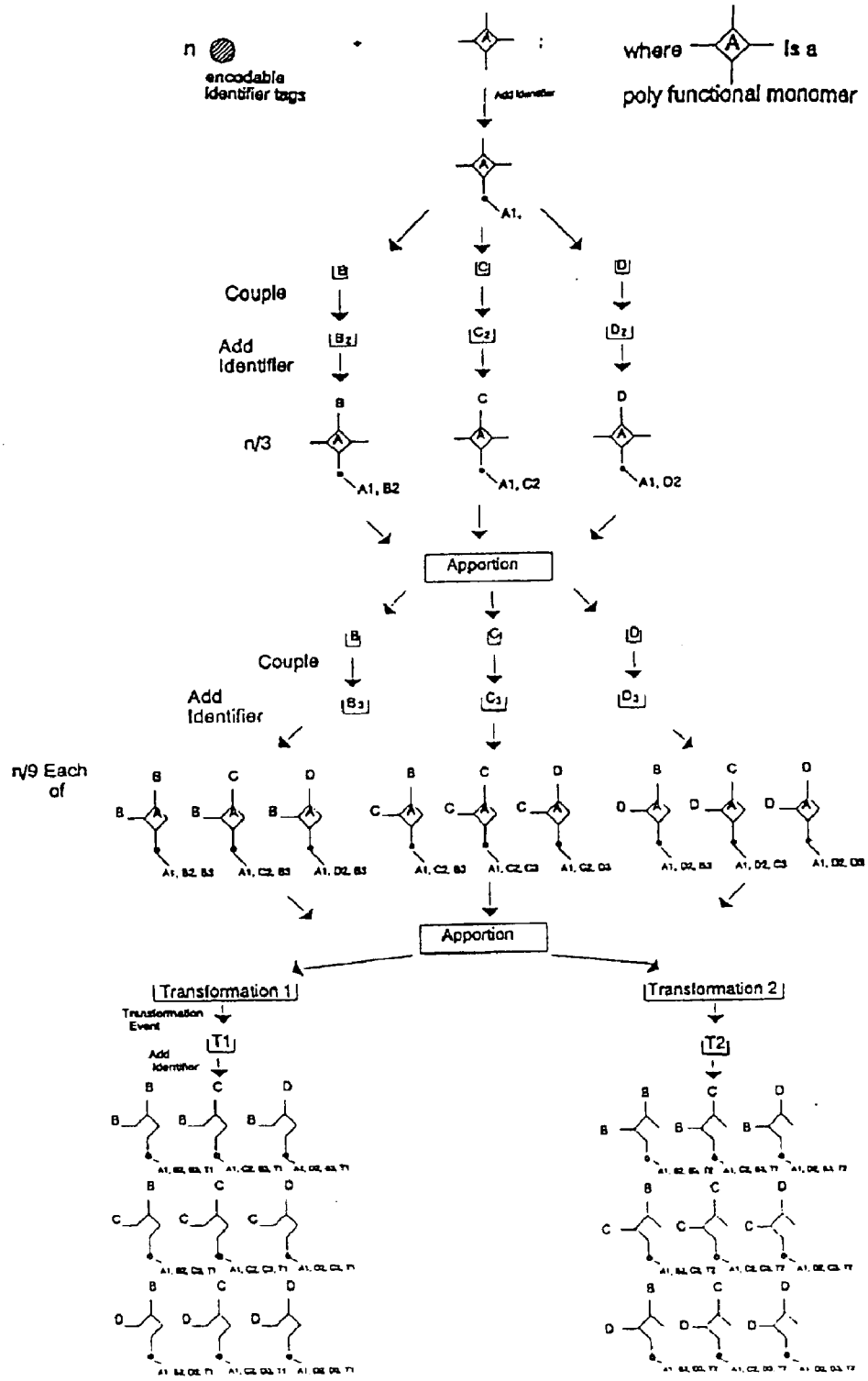
FIG. 6 schematically illustrates the synthesis of a labeled library oligomers constructed using a multiple cycle synthesis series with a plurality of different transformation events wherein the identifier tags are encoded in parallel with oligomer synthesis.

The parallel assembly of linear oligomers is shown schematically in FIGS. 1 and 2. The general method for parallel assembly of polypeptides can be illustrated by way of specific example. Twenty linker-derivatized ELAMS™, each having a unique identifier tag (Example III.A.) are placed in a reaction vessel and the sequence GGFL (SEQ ID NO:5) synthesized on each of the twenty ELAMS™ using standard Fmoc peptide synthesis reagents and chemistry as described in Atherton & Sheppard; Solid Phase Peptide Synthesis: A Practical Approach, IRL Press, Oxford, England (1989).

Following removal of the Fmoc groups by treatment with 30% piperidine in DMF for 60 min., the ELAMS™ are then apportioned into twenty reaction vessels, one ELAMS™ per vessel. Each vessel is then charged with a solution containing an amino acid monomer (0.1 M), HBTU (0.1 M), HOBt (0.1 M) and DIEA (0.1 M) in 9:1 methylene chloride:DMF for 30 min., a different amino acid monomer per vessel. The coupling may be repeated with fresh reagents for a further 30 min. The ELAMS™ are then washed with DMF (3×) and then with acetonitrile (3×). The identifier tag information is detected and recorded for each ELAMS™ in each reaction vessel, along with the identity of the monomer added. Side chain protecting groups are removed using standard deprotection chemistry. See Atherton & Sheppard, Solid Phase Peptide Synthesis: A Practical Approach, IRL Press, Oxford, England (1989), and the library assayed as described in Example II.F.

For libraries with larger diversity, successive rounds of coupling and identifier tag scanning and recording can be performed.

EXAMPLE IV

Parallel Synthesis of Oligonucleotide Octamers

A. Preparation of Hydroxyl ELAMS™

Sixteen ELAMS™, or multiples thereof, each having a unique identifier tag are cleaned in concentrated NaOH, followed by exhaustive rinsing in water. The ELAMS™ are derivatized for 2 hr with a solution of 10% (v/v) bis(2-hydroxyethyl)aminopropyltriethoxysilane (Petrarch Chemicals, Bristol, Pa) in 95% ethanol, rinsed thoroughly with ethanol (2×) and ether (2×), dried in vacuo at 40° C., and heated at 100° C. for 15 min.

B. Preparation of Linker

A synthesis linker, 4,4-dimethoxytrityl-hexaethyloxy-β-cyanoethyl phosphoramidite, can be prepared using 1,6-dihydroxyhexane as starting material according to the method of Beaucage and Caruthers, Atkinson and Smith, "Solid Phase Synthesis of Oligodeoxyribnucleotides by the Phosphite-Triester Method," in Gait, Oligonucleotide Synthesis: A Practical Approach, IRL Press, Oxford, England (1984) using 2-cyanoethyl N,N-diisopropylchlorophosphoramidite (Sigma, St. Louis, Mo.) as the phosphitylating reagent.

C. Attachment of Synthesis Linker

Synthesis linkers can be attached to ELAMS™ by reacting hydroxylated ELAMS™ (described in Example IV.A., above) with 4,4-dimethoxytrityl-hexaethyloxy-β-cyanoethyl phosphoramidite using standard phosphoramidite chemistry as described in Gait, Oligonucleotide Synthesis: A Practical Approach, IRL Press, Oxford, England (1984). Typical reaction conditions are 0.1 M phosphoramidite, 0.25 M tetrazole in anhydrous acetonitrile for 1–3 min. The ELAMS™ are rinsed with acetonitrile (3×).

Following coupling, any unreacted hydroxyl groups can be capped if desired. ELAMS™ are added to fresh capping solution which is prepared as follows: 3 volumes of a solution of 6.5% (w/v) 4-dimethylaminopyridine (DMAP) in anhydrous tetrahydrofuran (THF) are mixed with 1 volume of a solution of 40% (v/v) acetic anhydride in 2,6-lutidine. The reaction is allowed to proceed for 1–3 min., after which the ELAMS™ are rinsed with methylene chloride (2×) and acetonitrile (3×).

After capping, the phosphite triester bond is oxidized to a phosphotriester by treating the ELAMS™ with 0.1M iodine solution prepared by dissolving 2.6 g iodine in a mixture containing 80 mL THF, 20 mL 2,6-lutidine and 2 mL water for about 1 min. The ELAMS™ are rinsed with acetonitrile until the effluent is colorless.

The dimethoxytrityl groups protecting the hydroxyls can be removed by treatment with 2% (v/v) dichloroacetic acid (DCA) in methylene chloride for about 1 min. followed by rinsing (3×) with methylene chloride.: The number of hydroxyl groups per ELAMS™ (i.e. the loading capacity) can be determined by taking the absorbance of the dimethoxy trityl cation effluent at 498 nm ($\epsilon_{498}$=14,300 $M^{-1}$ $cm^{-1}$).

D. Preparation of Fluoresceinylated Probe

A target probe of sequence 5'-GCGCGGGC-fluorescein can be prepared using 3'-Amine-ON™ control pore glass (CPG) (Clontech, Palo Alto, Calif.) and standard DNA synthesis reagents (Applied Biosystems, Foster City, Calif.). The 3'-amine can be labeled with fluorescein isothiocyanate to generate a 3'-fluorescein labeled oligomer according to the manufacturer's instructions supplied with 3'-Amine-ON™ CPG.

E. Parallel Synthesis of Octanucleotides

Target oligomer sequences, represented by the matrix 3'-CGC$(A+T+C+G)^2$CCG can be prepared by synthesizing on each of sixteen linker-derivatized ELAMS™, each having a unique identifier tag (described in Example IIV.C.) polynucleotide sequence 3'-CGC using standard base-labile DNA synthesis reagents and chemistry (Applied Biosystems, Foster City, Calif.). Following the coupling cycle, the ELAMS™ are distributed into four reaction vessels, four ELAMS™ per vessel. A single nucleotide monomer (as the protected phosphoramidite) is coupled to the ELAMS™ in each reaction vessel using standard base-labile DNA synthesis reagents and chemistry, a different nucleotide monomer per vessel, and the capping, oxidation, and DMT removal steps completed.

The identifier tag from each ELAMS™ in each reaction vessel is detected and recorded using, for example, a model DAS-4001EM or model DAS-4001 scanner (Bio Medic Data Systems, Maywood, N.J.), along with the identity of each monomer added in each vessel. The ELAMS™ are then distributed by placing one ELAMS™ from each current reaction vessel into each of four new reaction vessels, and a second nucleotide monomer added as described above, a different monomer per vessel. The identifier information is detected and, recorded for each ELAMS™ in each reaction vessel, along with the identify of the monomer added in each vessel.

The ELAMS™ are then pooled into a single reaction vessel and the sequence 3-CCG added to each ELAMS™ using standard DNA synthesis reagents and chemistry. The exocyclic amine protecting groups are removed by treatment with conc. ammonia according to the manufacturer's instruction for base-labile nucleotide phosphoramidites.

EXAMPLE V

Sequence Specific Target Hybridization

The deprotected ELAMS™ are incubated with the fluoresceinylated probe under conditions conducive to sequence specific hybridization as described in Hames and Higgins, Nucleic Acid Hybridization: A Practical Approach, IRL Press, Oxford, England (1985). Following rinse cycles the ELAMS™ can be interrogated for hybridization using a fluorimeter or epifluorescence microscope (488-nm argon ion excitation). The ELAMS™ displaying the highest photon counts are isolated and the identifier tag scanned and compared to the reaction histogram for that particular identifier tag, revealing that the sequence 3'-CGCGCCCG was synthesized on the ELAMS™ displaying the highest photon count.

While the invention of this patent application is disclosed by reference to specific examples, it is understood that the present invention can be applied to all chemistries that are amenable to combinatorial strategies and to all identifier tags that relate information to a detector when pulsed with electromagnetic radiation. Further, the present invention is intended to be applicable to all future developed solid phase and multi-component combinatorial array syntheses, and to all future identifier tags that relate information to a detector when pulsed with electromagnetic information.

Accordingly, the invention may be embodied in other specific forms without departing from its spirit or essential characteristics. It is to be understood that this disclosure is intended in an illustrative rather than a limiting sense, as it is contemplated that modifications will readily occur to those skilled in the art, within the spirit of the invention and the scope of the appended claims.

SEQUENCE LISTING

```
<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Peptide

<400> SEQUENCE: 1

Tyr Gly Gly Phe Leu
  1               5


<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Peptide

<400> SEQUENCE: 2

Tyr Pro Gly Phe Leu
  1               5


<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Peptide

<400> SEQUENCE: 3

Pro Pro Gly Phe Leu
  1               5


<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Peptide

<400> SEQUENCE: 4

Pro Gly Gly Phe Leu
  1               5


<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Peptide

<400> SEQUENCE: 5
```

-continued

```
Gly Gly Phe Leu
  1


<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Peptide

<400> SEQUENCE: 6

Pro Gly Phe Leu
  1
```

What is claimed is:

1. A device for tracking synthesis of a library member of a combinatorial library, the device comprising:

a synthesis support having a surface adapted for linking to a first monomer;

an identifier tag disposed within or linked to the synthesis support, the identifier tag comprising encoded information readable by a radiofrequency scanner [or barcode scanner] that is unique to the synthesis support and means for scanning the identifier tag, wherein, when a first monomer is linked to the synthesis support, the first monomer and any oligomer synthesized using the first monomer is identified.

2. The device of claim 1 wherein the identifier tag comprises a microchip having an electronic memory within which is stored unique electronic information.

3. The device of claim 2 wherein the microchip comprises means for receiving and transmitting a radiofrequency signal.

4. The device of claim 2, wherein the microchip is encodable for recording synthesis information during synthesis of the library member.

5. The device of claim 4, wherein the synthesis information comprises descriptions of synthesis steps.

6. The device of claim 2, wherein the microchip is pre-encoded with an identification of the synthesis support.

7. The device of claim 2, wherein the microchip is encased in a glass or polymeric material.

8. The device of claim 7, wherein the polymeric material is derivatized with a functional group or linker.

9. The device of claim 8, wherein the polymeric material is selected from the group consisting of polystyrene-divinyl benzene, polyethylene-grafted polystyrene, polyacrylamide kieselguhr composite, and controlled pore glass.

10. The device of claim 8, wherein the linker is cleavable by a reaction selected from the group consisting of thermal, photochemical, electrochemical, oxidative, and reductive reactions.

11. The device of claim 3, wherein the microchip is powered by the radiofrequency signal.

12. The device of claim 2, wherein the unique electronic information is digitally encoded.

13. The device of claim 2, wherein the synthesis support is in a form selected from the group consisting of pellets, disks, capillaries, hollow fibers, solid fibers, cellulose beads, pore-glass beads, silica gels, polystyrene beads, grafted co-poly beads, poly-acrylimide beads, latex beads, dimethylacrylamide beads, and glass particles.

14. The device of claim 2, wherein the first monomer is linked to the synthesis support by a linker comprising a spacer residue.

[15. The device of claim 1, wherein the identifier tag comprises a bar code having unique information.]

[16. The device of claim 15, wherein the bar code is capable of receiving sequential synthesis information.]

[17. The device in claim 16, wherein the synthesis information comprises descriptions of synthesis steps.]

[18. The device of claim 15, wherein the barcode is pre-encoded with the identity of the synthesis support.]

[19. The device of claim 15, wherein the barcode is encased in a glass or polymeric material.]

[20. The device of claim 19, wherein the polymeric material is derivatized with a functional group or linker.]

[21. The device of claim 20, wherein the polymeric material is selected from the group consisting of polystyrene-divinyl benzene, polyethelene-grafted polystyrene, polyacrylamide kieselguhr composite, and controlled pore glass.]

[22. The device of claim 20, wherein the linker is cleavable by a reaction selected from the group consisting of thermal, photochemical, electrochemical, oxidative, and reductive reactions.]

* * * * *